United States Patent
Hei et al.

(10) Patent No.: US 6,436,445 B1
(45) Date of Patent: Aug. 20, 2002

(54) ANTIMICROBIAL AND ANTIVIRAL COMPOSITIONS CONTAINING AN OXIDIZING SPECIES

(75) Inventors: Robert D. P. Hei, Baldwin, WI (US); Kim R. Smith, Woodbury, MN (US); Polly D. Laugen, Minnetonka, MN (US); Shaun P. Kennedy, North Oaks, MN (US)

(73) Assignee: Ecolab Inc., St. Paul, MN (US)

( * ) Notice: Subject to any disclaimer, the term of this patent is extended or adjusted under 35 U.S.C. 154(b) by 0 days.

(21) Appl. No.: 09/277,592

(22) Filed: Mar. 26, 1999

(51) Int. Cl.$^7$ .............. A01N 33/02; A01N 59/12; A23L 3/3454; A61L 2/16; C11D 7/02
(52) U.S. Cl. .............. 424/667; 422/37; 424/669; 424/723; 426/532; 510/131; 510/161; 510/372; 510/373; 510/376; 510/384; 510/385; 510/391
(58) Field of Search .............. 514/642, 643, 514/77, 78, 315, 358, 554; 424/613, 616, 667, 668, 669, 670, 671, 672, 722, 723; 422/37; 426/326, 335, 532; 134/2, 22.13, 22.14, 22.16, 42; 252/186.43, 187.2; 510/131, 132, 161, 219, 234, 372, 373, 376, 384, 385, 391

(56) References Cited

U.S. PATENT DOCUMENTS

| | | | |
|---|---|---|---|
| 2,193,636 A | 3/1940 | Marshall | 99/156 |
| 2,512,640 A | 6/1950 | Greenspan et al. | 99/154 |
| 2,662,855 A | 12/1953 | Kamlet | 210/28 |
| 2,666,010 A | 1/1954 | Stayner | 167/30 |
| 2,679,533 A | 5/1954 | Darragh et al. | 260/567.6 |
| 2,692,231 A | 10/1954 | Stayner et al. | 210/23 |
| 2,740,744 A | 4/1956 | Abramitis et al. | 167/38 |
| 2,746,928 A | 5/1956 | Darragh et al. | 252/106 |
| 2,751,713 A | 6/1956 | Abramitis | 47/58 |
| 2,863,798 A | 12/1958 | Shelanski et al. | 167/17 |
| 2,868,686 A | 1/1959 | Shelanski et al. | 167/17 |
| 2,917,428 A | 12/1959 | Hitzman | 167/22 |
| 3,152,073 A | 10/1964 | Morton | 210/62 |
| 3,194,758 A | 7/1965 | Lissant | 210/54 |
| 3,223,643 A | 12/1965 | Law | 252/106 |
| 3,344,018 A | 9/1967 | Shibe, Jr. et al. | 167/22 |
| 3,380,923 A | 4/1968 | Beach | 252/106 |
| 3,525,696 A | 8/1970 | Schmidt et al. | 252/106 |
| 3,749,673 A * | 7/1973 | Jones | 252/95 |
| 3,778,476 A | 12/1973 | Rembaum et al. | 260/567.6 |
| 3,898,336 A | 8/1975 | Rembaum et al. | 424/25 |
| 3,958,020 A | 5/1976 | Devries | 426/265 |
| 3,966,090 A | 6/1976 | Prussin et al. | 424/47 |
| 4,045,176 A | 8/1977 | Ramachandran | 252/8.5 |
| 4,051,058 A | 9/1977 | Bowing et al. | 252/186 |
| 4,051,059 A | 9/1977 | Bowing et al. | 252/186 |
| 4,073,888 A | 2/1978 | Snyder | 424/149 |
| 4,111,679 A | 9/1978 | Shair et al. | 71/67 |
| 4,113,857 A | 9/1978 | Shetty | 424/150 |
| 4,206,233 A | 6/1980 | Quinlan | 424/329 |
| 4,336,152 A | 6/1982 | Like et al. | 252/106 |
| 4,397,757 A | 8/1983 | Bright et al. | 252/186.1 |
| 4,592,488 A * | 6/1986 | Simon | 222/94 |
| 4,597,975 A | 7/1986 | Woodward et al. | 424/150 |

(List continued on next page.)

FOREIGN PATENT DOCUMENTS

| | | |
|---|---|---|
| DE | 18 13 584 | 10/1969 |
| DE | 28 21 199 | 11/1978 |
| DE | 29 05 373 | 9/1979 |
| DE | 41 37 544 A1 | 5/1993 |
| EP | 0 086 423 A2 | 8/1983 |
| EP | 0 087 049 A1 | 8/1983 |
| EP | 0 095 377 A1 | 11/1983 |
| EP | 0 156 646 A1 | 10/1985 |
| EP | 0 185 970 A1 | 7/1986 |
| EP | 0 214 850 A2 | 3/1987 |
| EP | 0 443 640 A2 | 8/1991 |
| EP | 4-082959 | 3/1992 |
| EP | 0 832 964 A1 | 4/1998 |
| EP | 1 001 012 A1 | 5/2000 |
| FR | 2663852 | 1/1992 |
| GB | 898820 | 6/1962 |
| GB | 1 265 919 | 3/1972 |
| GB | 1301861 * | 1/1973 |
| GB | 1 301 861 | 1/1973 |
| GB | 1346594 | 2/1974 |
| GB | 2132087 A | 7/1984 |
| GB | 2 268 879 | 1/1994 |
| JP | 4-107223 | 4/1992 |
| JP | 4-321627 | 11/1992 |
| WO | WO 88/00795 | 2/1988 |
| WO | WO 88/02351 | 4/1988 |
| WO | WO 93/17693 | 9/1993 |
| WO | WO 94/00548 | 1/1994 |
| WO | WO 96/14092 | 5/1996 |
| WO | WO 97/34834 | 9/1997 |

OTHER PUBLICATIONS

Abdelkader, M. et al., "Spectrophotometric Analysis of Quaternized Drugs", *Die Pharmazie*, pp. 30–32 (1980).

Chowdhury, A.N. et al., "Improved Rapid Determination of Nickel in Soils and Laterites", *Analytical Chemistry*, pp. 820–821 (Jun. 1960).

Darrow, R. et al., "An Improved spectrophotometric triiodide assay for lipid hydroperoxides", *Chemical Abstracts*, vol. 121, No. 15, Abstract No. 121:174365e, pp. 546–547 (Oct. 10, 1994).

*Primary Examiner*—Jeffrey E. Russel
(74) *Attorney, Agent, or Firm*—Merchant & Gould P.C.

(57) ABSTRACT

An oxidizing species is described herein as a reaction product through an in situ preparation combining a quaternary or protonizable nitrogen compound, an oxidant compound and a halide source at controlled proportions in an aqueous, non-aqueous, gel, aerosol, solid-phase or powdered media. The oxidizing species can be used to reduce microbial and viral populations on a surface or object or in a body or stream of water. The invention thus finds applications as a bleach, sanitizer, oxidant, or in any other application in which an oxidizing agent can be beneficially used alone or in a formulation.

3 Claims, No Drawings

U.S. PATENT DOCUMENTS

| | | | |
|---|---|---|---|
| 4,654,208 A | 3/1987 | Stockel et al. | 424/78 |
| 4,704,212 A | 11/1987 | Schindler et al. | 252/8.8 |
| 4,737,307 A | 4/1988 | Brown et al. | 252/106 |
| 4,741,851 A | 5/1988 | Borrello | 252/91 |
| 4,804,492 A | 2/1989 | Bernarducci | 252/106 |
| 4,822,513 A | 4/1989 | Corby | 252/106 |
| 4,824,867 A | 4/1989 | Smith et al. | 514/642 |
| 4,857,223 A | 8/1989 | Borrello | 252/91 |
| 4,874,788 A | 10/1989 | Smith et al. | 514/534 |
| 4,900,721 A | 2/1990 | Bansemir et al. | 514/25 |
| 4,937,072 A | 6/1990 | Kessler et al. | 424/94.4 |
| 4,941,989 A | 7/1990 | Kramer et al. | 252/106 |
| 4,960,590 A | 10/1990 | Hollis et al. | 424/78 |
| 4,976,874 A | 12/1990 | Gannon et al. | 210/755 |
| 5,047,164 A | 9/1991 | Corby | 252/106 |
| 5,070,105 A | 12/1991 | Segall et al. | 514/626 |
| 5,081,106 A | 1/1992 | Bentley et al. | 514/5 |
| 5,093,078 A | 3/1992 | Hollis et al. | 422/16 |
| 5,117,049 A | 5/1992 | Venturello et al. | 562/2 |
| 5,200,189 A | 4/1993 | Oakes et al. | 424/616 |
| 5,202,047 A | 4/1993 | Corby | 252/106 |
| 5,264,191 A | 11/1993 | Nakao et al. | 423/22 |
| 5,320,805 A | 6/1994 | Kramer et al. | 252/106 |
| 5,366,983 A | 11/1994 | Lattin et al. | 514/358 |
| 5,545,349 A * | 8/1996 | Kurii | 252/186.38 |
| 5,576,282 A | 11/1996 | Miracle et al. | 510/276 |
| 5,620,527 A | 4/1997 | Kramer et al. | 134/2 |
| 5,658,467 A | 8/1997 | LaZonby et al. | 210/754 |
| 5,683,724 A | 11/1997 | Hei et al. | 424/616 |
| 5,756,090 A | 5/1998 | Allen | 424/94.4 |
| 6,106,854 A * | 8/2000 | Belfer | 424/405 |

\* cited by examiner

ANTIMICROBIAL AND ANTIVIRAL COMPOSITIONS CONTAINING AN OXIDIZING SPECIES

FIELD OF THE INVENTION

The invention relates to antimicrobial and antiviral compositions containing an oxidizing species. The materials are made by reacting cooperating ingredients at controlled proportions to form an oxidant that can have a variety of end uses. The oxidizing species of the invention is an in situ generated oxidant stable for limited periods, typically less than a few days.

BACKGROUND OF THE INVENTION

Peroxygen sanitizers and halogen sanitizers are known. Peroxygen sanitizers include compounds such as hydrogen peroxide, percarboxylic acids, percarbonates, perborates, etc. These materials are relatively well characterized and understood and are commonly used in a variety of end uses. Halogen sanitizers include compounds such as hypochlorite (HOCl), chlorine dioxide ($ClO_2$), perchlorate ($HClO_4$), perbromate ($HBrO_4$), and others. These materials also have relatively well characterized compositions and properties. Halide and quaternary ammonium base sanitizers are also known. These materials are generally not considered oxidizing materials but provide sanitizing properties to materials. One type of halogen based sanitizers are sanitizers that can contain species such as $I_3^{-1}$, $IBrCl^{-1}$, and other similar species. Representative examples of such materials include Rembaum et al., U.S. Pat. No. 3,898,336; Rembaum et al., U.S. Pat. No. 3,778,476; Hollis et al., U.S. Pat. No. 4,960,590; Hollis et al., U.S. Pat. No. 5,093,078 and Dammann, European patent application No. 156646. These references describe isolated polymeric quaternary ammonium polyhalides based on synthetic polymeric ionene (known in the industry as polymeric quats), epi-amine, and cationic acrylamide polymer resins (containing 2 or more cationic groups) precipitated with polyhalogens. Similarly, Corby, U.S. Pat. No. 4,822,513; Corby, U.S. Pat. No. 5,047,164; and Corby, U.S. Pat. No. 5,202,047 describe mixed interhalogen salts limited to 4 halogens with a maximum of one iodine or bromine atom per complex. Also, Kramer et al., U.S. Pat. No. 4,941,989; and Kramer et al., U.S. Pat. No. 5,620,527 describe the use of antimicrobial compositions made of alkaline per-salts of quaternary ammonium compounds and hydroperoxide (i.e., $HOO^-$) anions at pH's of greater than 9.5. No polyhalide counterions are utilized. Asensio, EP 0 799 570 A1 discloses a five component antimicrobial mix containing two quaternary tri-iodides (prepared via conventional molecular halogen addition, not by in-situ reaction). LaZonby, et al., U.S. Pat. No. 5,658,467 describes the use of peracetic acid in combination with a non-oxidizing biocide for industrial process waters. Lastly, Wright et al., PCT Application No. WO 94/00548 describes non-halogen containing quaternary ammonium compounds which are used with peracids, preferably peracetic acid. This disclosure indicates that the peracid material is activated by the presence of the quaternary ammonium compound.

None of the aforementioned references teach the use of in-situ, labile antimicrobial compositions generated via halide salts and oxidants; especially peroxygen oxidants. All of these examples deal with stable, isolated antimicrobials that would remain in the application environment (e.g., food surface) indefinitely. Lastly, Wright et al., PCT Application No. WO 94/00548 describes non-halogen containing quaternary ammonium compounds which are used with peracids, preferably peracetic acid. This disclosure indicates that the peracid material is activated by the presence of the quat.

SUMMARY OF THE INVENTION

We have discovered a synergistic effect resulting from the combination of a source of quaternary or protonizable nitrogen, an oxidant, preferably a peroxygen compound, and a halide source, for example, an elemental halogen(s), or metal or ammonium halide salt(s), preferably including an iodide salt. More specifically, we have found that a synergistic oxidizing species is created from this combination. Since reaction is almost immediate, an in-situ aqueous or non-aqueous use solution can be available for use immediately after mixing as an antimicrobial or antiviral composition; or the active composition can be stabilized and post-incorporated into a non-aqueous liquid, gel, aerosol, powder, or solid formulation.

It is also possible to produce solid sanitizing substrates containing this oxidizing species that have residual antimicrobial and antiviral effectiveness; such as in air filters or as packaging or plastic or as cutting board additives.

Accordingly, the invention resides in a complex for antimicrobial or antiviral use, the complex being the product of an in-situ reaction of a source of a quaternary or protonizable nitrogen compound, an oxidant, and a halide source. The invention also resides in the use of said complex to reduce microbial or viral populations on a surface or object or in a body or stream of water. Thus, this in-situ species is effective in reducing microbial and viral populations on hard surfaces (such as glass, ceramics, metal, natural and synthetic rock, wood, and polymeric), elastomers and plastics, woven and non-woven substrates. More specifically, the compositions containing the complex are shown to be effective antimicrobial and antiviral agents for sanitizing and disinfecting surfaces and air streams typically encountered in hospital, surgical, infirmity, birthing, mortuary, and clinical diagnosis rooms. These surfaces can be those typified as "hard surfaces" (such as walls, floors, bed-pans, etc.), or woven and non-woven surfaces (such as surgical garments, draperies, bed linens, bandages, etc.), or patient-care equipment (such as respirators, diagnostic equipment, shunts, body scopes, etc.), or a plethora of surgical and diagnostic equipment.

The complex can also be used to reduce odors and microbial or viral populations in gaseous streams, bleaching of or reducing microbial or viral populations on woven or non-woven substrates, and treating skin diseases of, or on, mammals; i.e., in treating skin diseases on animals (especially mammals), or those which spread via transfer to air or surface substrates, such as disease from fungi, bacteria and viruses. The complex can also be used to reduce microbes and odors in animal feeds, in animal watering stations and enclosures, in animal veterinarian clinics, animal surgical areas, and to reduce animal or human pathogenic (or opportunistic) microbes and viruses on animals. The complex can also be used to reduce opportunistic pathogenic microbes on living eggs.

Additionally, the compositions containing the complex are effective by themselves, or mixed with other adjuvants, in reducing microbial and viral populations in applications in the food industry. These include food preparation equipment, belt sprays for food transport lines, boot and hand-wash dip-pans, food storage facilities and anti-spoilage air circulation systems, aseptic packaging sanitizing, food refrigeration and cooler cleaners and sanitizers, warewashing sanitizing, blancher cleaning and sanitizing, food packaging materials, cutting board additives, third-sink sanitizing, beverage chillers and warmers, meat chilling or scalding waters, sanitizing gels, food processing antimicrobial garment sprays, and non-to-low-aqueous food preparation lubricants, oils, and rinse additives.

The invention also resides in a concentrated antimicrobial and antiviral species including in composition the product of an in-situ reaction of a source of quaternary or protonizable nitrogen, an oxidant, preferably a peroxygen compound, and a halide source. The reaction may be conducted in an aqueous, non-aqueous, gel, aerosol, or solid-phase or powdered media, and for each part by weight of the halide source there is about 0.1 to 30 parts by weight of the nitrogen compound, about 0.1 to 40 parts by weight of the oxidant compound. In an aqueous solution, the composition has a pH of less than about 9.5.

The invention further resides in an aqueous, in-situ, antimicrobial and antiviral composition containing the combination of: (a) a source of quaternary or protonizable nitrogen; (b) an oxidant, preferably a peroxygen compound; (c) a halide source, e.g., a metal or ammonium halide salt(s), halogens, or organo-halides; and (d) the balance being water. Preferably, for each part by weight of the halide source there is about (a) 0.1 to 80 weight percent (wt-%), preferably about 1 to 15 wt-%, of a source of a quaternary or protonizable nitrogen source (most preferably a quaternary ammonium, protonized amine, amine oxide, or amphoteric surfactant source); (b) about 0.1 to 75 wt-%, preferably about 1 to 20 wt-% of an oxidant (preferably a peroxygen) compound; and (d) the balance being water. In a diluted form, this use solution will contain about 0.1 to 200,000 parts per million (ppm), preferably 5 to 10,000 ppm, and most preferably 10 to 100 ppm of the halide source.

The invention further resides in a mixable, at the point of use, two-part liquid concentrate antimicrobial and antiviral composition having in one part: about 0.1 to 80 wt-% preferably about 1 to 15 wt-%, of a source of a quaternary or protonizable nitrogen compound, about 0.1 to 75 wt-%, preferably about 1 to 20 wt-%, of an oxidant, and the balance being water; and in the second part: about 0.1 to 80 wt-% of a halide source, preferably about 1 to 15 wt-%, and the balance being water. Various inerts and surfactants may be added to either part.

Also, the invention resides in an antimicrobial and antiviral composition suitable for subsequent incorporation into solid, gel, aerosol, or non-aqueous liquid cleaning, sanitizing, or disinfecting products for treatment of surfaces. Thus, these include in powder, liquid, gel, or solid form: a) a source, preferably a natural one, of a quaternary or protonizable nitrogen compound; (b) an oxidant, preferably a peroxygen compound or oxidizing gas; (c) a halide source; and optionally (d) a source of acidity; wherein for each part by weight of the halide source there is about 0.1 to 30 parts by weight of the nitrogen compound, about 0.1 to 40 parts by weight of the oxidant compound, unless an oxidizing gas is used to form the complex in-situ and, then, an excess of the oxidant can be employed. The antimicrobial or antiviral composition is incorporated into the cleaning, disinfecting, or sanitizing substrate at a level of about 0.001 to about 95 weight %.

The invention also resides in said powder antimicrobial or antiviral compositions suitable for incorporation (casting, absorbing, adsorbing, spray-drying, etc.,) into solid, elastomeric, or fibrous substrates for residual antimicrobial or antiviral effects.

The invention also resides in antimicrobial or antiviral compositions comprising a combination of (a) a quaternary or protonizable nitrogen compound, preferably a natural source, with (b) a polyhalogen-containing anion, and (c) a water-soluble or dispersible substrate which greatly improves the solubility or efficacy of said complexes.

The invention further resides in a process for preparing a solvent-free liquid, powdered, or solid-phase antimicrobial or antiviral complex including applying or generating heat, gaseous water vapor, or chemical hydrates, to a mixture of a solid, gel, or powder composition containing a source of a quaternary or protonizable nitrogen compound, an oxidant, and a halide source; and cooling the resulting complex to ambient temperature. It also encompasses solvent-free liquid complexes prepared by such a method.

The invention also resides in treating food processing or transport waters with said liquid, gel, solid, or powdered compositions.

The invention additionally resides in treating food processing equipment and/or ware, (e.g. utensils, dishware, washware,) with said liquid, gel, aerosol, solid, or powdered compositions, or solutions containing these compositions.

The invention additionally resides in sanitizing third-sink rinse waters and utensils (e.g. bar glasses) with said liquid, gel, solid, or powdered compositions.

The invention additionally resides in treating animal quarters, surgical or treatment areas, in animal feeds, or animal carcasses; with said compositions.

The invention additionally resides in treating air streams with said compositions.

DETAILED DISCUSSION OF THE INVENTION

The invention involves a complex for antimicrobial or antiviral use, including the product of the in-situ, i.e., in place, reaction of a source of quaternary or protonizable nitrogen, an oxidant, preferably a peroxygen compound and, a halide or halogen source, e.g., a metal or ammonium halide salt; wherein the reaction is conducted in an aqueous, non-aqueous, gel, aerosol, solid phase or powdered media. Preferably, for each part by weight of the halide source there is about 1 to 10 parts by weight of the source of quaternary or protonizable nitrogen, and about 1 to 10 parts by weight of the oxidant, preferably peroxygen compound. In an aqueous reacted solution, or in a use solution, the pH is about 9.5 or less.

The complex of the invention may be prepared from the in-situ reaction being carried out in water, a non-aqueous liquid, a gel, or aerosol. Alternately, another process lies in the in-situ reaction in a powder or solid state with water vapor or hydrating compounds present; while yet another process may be carried out with an oxidizing gas passing into the powder or solid or a non-aqueous liquid.

Nitrogen Sources

Typically, the quaternary nitrogen compound can be a quaternary ammonium compound having the formula:

(I)

wherein X is an anion except a hydroperoxide anion, and R, R', R" and R'" are each independently a straight or branched, unsaturated or saturated, hydrocarbon group of 1 to 24 carbon atoms, in which the hydrocarbon chain is unsubstituted or substituted by hydroxyl, carboxyl, or alkylamido, or in which the hydrocarbon chain is uninterrupted or interrupted by a heteroatom; an aryl group, or aralkyl group in which alkyl has 1 to 4 carbon atoms. One embodiment of the formula I includes a compound where R' is benzyl and R" is aryl or benzyl.

An alkyl group is defined as a paraffinic hydrocarbon group which is derived from an alkane by removing one hydrogen from the formula. The hydrocarbon group may be linear or branched. Simple examples include methyl ($CH_3$) and ethyl ($C_2H_5$). However, in the present invention, at least one alkyl group may be medium or long chain having, for example, 8 to 16 carbon atoms, preferably 12 to 16 carbon atoms.

An alkylamido group is defined as an alkyl group containing an amide functional group: $-CONH_2$, $-CONHR$, $-CONRR'$.

A heteroatom is defined as a non-carbon atom which interrupts a carbon chain. Typical heteroatoms include nitrogen, oxygen, phosphorus, and sulfur.

An aryl group is defined as a phenyl, benzyl, or naphthyl group containing 6 to 14 carbon atoms and in which the aromatic ring on the phenyl, benzyl or naphthyl group may be substituted with a $C_1$-$C_3$ alkyl. An aralkyl group is aryl having an alkyl group of 1 to 4 carbon atoms.

Certain quaternary nitrogen compounds are especially preferred. These include alkyl trimethyl ammonium salts, dialkyl dimethyl ammonium salts, alkyl dimethyl piperidinium salts, and alkyl dimethyl pyridinium salts.

The nitrogen compound can also be of the formula:

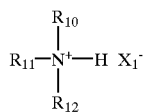

(II)

wherein $X_1$ is an anion; and $R_{10}$, $R_{11}$ and $R_{12}$ are each, independently, hydrogen or at least one straight or branched, saturated or unsaturated, hydrocarbon group of 1 to 24 carbon atoms, in which the hydrocarbon chain is unsubstituted or substituted by hydroxyl, carboxyl, or alkylamido, or in which the hydrocarbon chain is uninterrupted or interrupted by a heteroatom; an aryl group, or aralkyl group in which alkyl has 1 to 4 carbon atoms.

Several preferred compounds are shown below. The first structure shown is cetyl trimethyl ammonium chloride, which is an example of formula I; the second structure, dodecyl dimethyl ammonium hydrochloride, is an example of formula II, and the third is didecyl dimethyl ammonium chloride, another example of formula I:

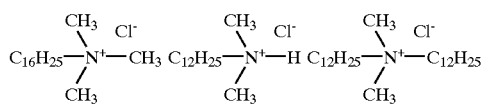

In each structure, the ammonium nitrogen is seen as covalently bonded to four substituents and ionically bonded to a chlorine anion.

In the invention, the quaternary ammonium cation can also be generated from an amphoteric molecule. An amphoteric compound can function as either an acid or as a base, depending on its environment, and has both functional groups present. A representative structure of the cation generated from an amphoteric molecule is shown below:

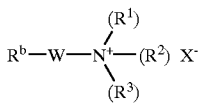

(III)

wherein W is a linear or branched alkylene, hydroxyalkylene or alkoxyalkylene group having 1–6 carbon atoms;

$R^b$ is $R^4-CO-NH$ in which $R^4$ is a saturated or unsaturated, branched or linear hydrocarbon group having 4–22 carbon atoms, or $R^4$;

$R^1$ is hydrogen, A or $(A)_n-W-CO_2^-M^+$ in which A is a linear or branched alkyl, hydroxyalkyl or alkoxyalkyl having 1–4 carbon atoms, n is an integer from 0 to 6, and M is an alkali metal cation, a hydrogen ion or an ammonium cation;

$R^2$ is $(A)_n-W-CO_2^-M^+$;

$R^3$ is hydrogen or A; and

X is an anion.

An example of a suitable amphoteric is shown below:

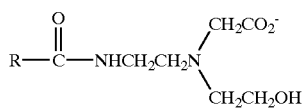

where R is hydrogen, straight or branched alkyl having 1 to 16 carbon atoms, in which the alkyl group is uninterrupted or interrupted by phenyl. This is not itself a quaternary ammonium compound. Treatment with an organic or inorganic acid $H^+X^-$ can result in a compound of the formula:

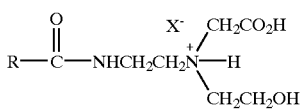

where $X^-$ is an anion. This does indeed represent a quaternary ammonium compound which can be mixed with an appropriate oxidant and halogen, or halide salt, to meet the claimed invention, wherein.

Another class of amphoteric compounds can include the phosphorus containing species such as phospholipids like the lecithins (including phosphatidyl choline.), sphingomyelin, and the cephalins. Or modified phosphoamphoterics such as the Phosphoterics®, sold by Mona Industries.

The invention can also use protonizable nitrogen sources. Examples include proteins, amino acids, amine oxides and amines which can form acid salts and mixtures thereof. These include, for example, sarcosine, taurine, glycine, and simple proteins such as albumins, phosphoproteins, protamines, histones, chromoproteins, schleroproteins, glutenins and globulins. Examples of protonizable proteins include milk, egg, blood and plant proteins. The nitrogen compound can be a protein, an acid salt thereof, or a mixture Of proteins and their corresponding acid salts. Generally, these can be characterized as:

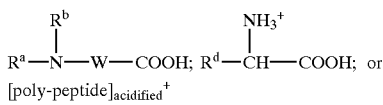

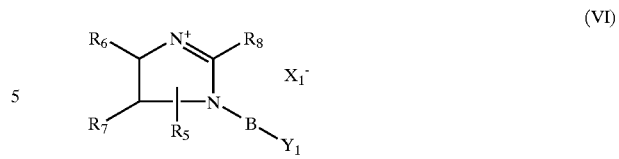

wherein $R^a$ is a linear or branched, saturated or unsaturated, hydrocarbon, hydroxyalkyl or alkoxyalkyl group having 1–22 carbon atoms; $R^b$ is H or $CH_3$, and W is a linear or branched alkylene, hydroxyalkylene or alkoxyalkylene group having 1–4 carbon atoms.

$R^d$ is a common moiety as part of natural amino acids; e.g., H, alkyl, hydroxyalkyl, thioalkyl, alkyl-aryl, carboxyl, amido, alkyl-amino, and the like.

[poly-peptide]$_{acidified}^+$ refers to an acidified polypeptide, such as an acidified protein.

Additional preferred quaternary nitrogen sources include a choline, particularly a choline chloride, a choline bitartrate, an acetyl choline; or mixtures thereof. An additional preferred compound is cetyl dimethyl pyridinium chloride. The nitrogen source may also include mixtures thereof.

The nitrogen compound can also be a betaine, sultaine or phosphobetaine of the formula

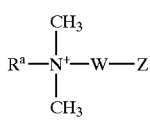

(IV)

wherein Z is $CO_2H$, $CO_2^-$, $SO_3H$, $SO_3^-$, $OSO_3H$, $OSO_3^-$, $OPO_3H$ or $OPO_3^-$; W is a linear or branched alkylene, hydroxyalkylene or alkoxyalkylene group having 1–6 carbon atoms; and $R^a$ is a linear or branched alkyl, hydroxyalkyl or alkoxyalkyl group having 1–22 carbon atoms; or $R^4$—CO—NH(CH$_2$)$_{x'}$ in which $R^4$ is a saturated or unsaturated, branched or linear hydrocarbon group having 4–22 carbon atoms, and x' is an alkylene group having 1–6 carbon atoms.

A suitable betaine cation is shown below:

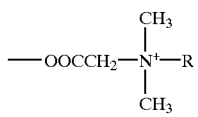

wherein; R is a linear or branched alkyl, hydroxyalkyl or alkoxyalkyl group having 1–22 carbon atoms; or $R^4$—CO—NH(CH)$_x$ in which $R^4$ is a saturated or unsaturated, branched or linear hydrocarbon group having 4–22 carbon atoms, and x is an alkylene group having 1–6 carbon atoms. Of special interest is the natural product betaine where R has 1 carbon atom.

In another embodiment, the nitrogen compound can be of the formula:

wherein $R_6$, $R_7$ and $R_8$ are each, independently, H or —$A_1$—Y in which $A_1$ is a $C_7$ to $C_{20}$ saturated or unsaturated, linear or branched alkylene group, and Y is H, $NH_2$, OH or COOM$_1$, in which $M_1$ is H or a Group I metal ion;

B is a $C_1$ to $C_{20}$ saturated or unsaturated, linear or branched chain alkylene group, and $Y_1$ is H, $NH_2$, OH, COOM$_2$ or —NH—COR$_q$ in which $M_2$ is H or a Group I metal ion and R$_q$ is a $C_1$ to $C_{20}$ saturated or unsaturated, linear or branched chain alkyl group;

$R_5$ is H or a $C_1$ to $C_3$ alkyl group at one of the nitrogen atoms; and $X_1^-$ is an anion.

Typical imidazolines are: coconut hydroxyethyl imidazoline, tall oil aminoethyl imidazoline, oleyl hydroxyethyl imidazoline, the Miramines®, the Rhodaquats®, the Monazolines®, the Rewoterics®, the Crodazolines®, available from Mona Industries Inc., Rhone Poulenc, Rewo Chemische Werke GmbH, and Croda Surfactants Ltd.

Oxidants

In addition to the source of quaternary or protonizable nitrogen, an oxidizing agent is also necessary. It is possible to utilize oxidants such as hypochlorites, chlorates, chlorites, permanganates, nitrates, or nitric acid, etc.; or gaseous oxidants such as ozone, oxygen, chlorine dioxide, chlorine, sulfur dioxide, etc. Preferred compounds include peroxides and various percarboxylic acids, including percarbonates. The preferred peroxygen compound is hydrogen peroxide, peracetic acid, or a percarbonate. The percarbonate can be formed in situ as a mixture of hydrogen peroxide and sodium bicarbonate. Percarboxylic acids may also be formed in situ by use of a combination of hydrogen peroxide and the desired carboxylic acid. For solid compositions, the use of percarbonates, perborates, persulfates, etc., are useful; especially where the backbone substrate (e.g., carbonate) itself is not essentially oxidized but instead acts as a substrate for the peroxygen complex. Most preferred is sodium percarbonate in solid formulations; however, gaseous oxidants are useful for non carbonate containing compositions. For liquid compositions, hydrogen peroxide or peracetic acid are the preferred oxidants; however, hypochlorites, chlorites, or ozone might also be employed for in-situ preparations. Ultimately, any oxidant that can convert the halide source into its complexed form is acceptable.

Halides

There are a large number of possible halide sources useful in the present invention such as metal or ammonium halides, haloforms or other organic halogens, or elemental halogens. Preferred metal halides include alkali metal iodide salts of the formula MI$_n$, and MBr$_n$ wherein M is a metal ionic species and n is a number equal to the metal valence. Preferred alkali metals are sodium and potassium. Other preferred halides include bromides and chlorides. A preferred embodiment uses a metal halide salt which includes a mixture of halide salts containing at least one iodide salt. The alkali metal is preferably sodium or potassium. Another preferred embodiment uses a single metal halide salt which is an iodide or bromide salt. A preferred salt is potassium iodide, cuprous iodide or a mixture thereof. Also useful are sources containing halides such as sea water, kelp, table salt, etc.

Acids

The invention can also include, if necessary, an acid component for controlling the use solution pH. This may be necessary for non-permanent quaternary ammonium compounds (i.e., amphoteric, amine oxides, amines, proteins, amino acids) to enhance microbial reduction; probably because the unquaternized amine compound must be in its cationic or slightly neutralized form to form the labile, in-situ complex. The exact pH necessary will depend on the identity of the amine involved but, preferably, should be about 9.5 or less, preferably less than about 8.5.

Mineral and organic acids are useful for pH adjustment. The acid source might, for example, be an inorganic-based acid such as phosphoric, sulfuric, hydrochloric, nitric, sulfamic; or organic-based such as malic acid, tartaric acid, citric acid, acetic acid, glycolic, glutamic acid, sorbic acid, benzoic acid, succinic acid, or dimer and fatty acids; or mixtures thereof. Alternatively, the source of acidity can include an acid salt such as sodium diacetate, monobasic potassium or sodium phosphate. Additionally, carbonation acidification via the interaction of carbon dioxide with water is possible for aqueous formulations.

Besides the aforementioned cationic and amphoteric surfactants for the active complex formation, the invention also includes standard nonionic, anionic, cationic, or amphoteric compounds for surface tension reduction, wetting, and detersiveness. For example, linoleic acid, alkyl glycosides, alcohol ethoxylates, nonylphenol ethoxylates, alkanolamides, alkylbenzene sulfonates, petroleum sulfonates, diphenylether sulfonates, alpha-olefin sulfonates, stearyl citrate, alkyl naphthalene sulfonates, Pluronics® and various short-chain fatty acids are all readily useful. The wetting agents are typically not necessary for affecting the microbial reduction, but are present for detersive and surface tension reduction reasons; however, some may be employed as part of the synergistic, in-situ, antimicrobial formula.

Likewise, inerts might be added as fillers, buffers, chelants, anticaking agents, etc. For example, formulations have been prepared with: sodium chloride, bicarbonates, sulfates, silicates, phosphates, cellulosic derivatives, and EDTA.

It is believed that the working compound in the composition of the invention is a poly-halogen salt of the quaternary ammonium cation. The poly-halogen salt can include an anion of the formula $I_wBr_yCl_{y1}F_z$, wherein w is an integer from 1 to 8, y and $y_1$, are each independently integers from 0 to 8, and z is an integer from 0 to 1. In a typical reaction, for example, a quaternary ammonium compound reacts with potassium iodide in the presence of an oxidizing agent to produce the poly-halogen salt. If only KI is used, the poly-halogen anion is represented by $I_w$, where w ranges from 1 to 8. If KBr is also added to the reaction mixture, the resulting interhalogen anion is represented by $I_wBr_y$, where w plus y equals 2 to 9. If a quaternary ammonium chloride is used the reaction with potassium iodide in the presence of an oxidizing agent would produce an inter-halogen salt; however, in contrast to other known interhalogens containing three or less halogen atoms the current art contains 4 or more. While an inorganic metal bromide is optional in the reaction mixture, the inorganic metal or ammonium iodide is not. The product requires the presence of at least some inorganic metal or ammonium iodide.

The aqueous solution of the invention, made by the in-situ reaction or by addition of the pre-made complex to a solution, is characterized by a yellow to red color which serves as an indicator of solution effectiveness. As long as the color remains, the solution retains good killing properties. The effective time period is about 50 hours. Generally for unbuffered or non-acidic formulations, as the reaction takes place, the pH of the solution increases from about 5 to about 10. At the same time, the oxidation/reduction potential (ORP) increases accordingly. This is noteworthy since ORP normally is in inversely proportional to pH and, thus, indicates a very active oxidizing species being formed. According to the claimed invention, use solutions are aqueous solutions containing a source of quaternary or protonizable nitrogen ammonium compound, an oxidant which is preferably a peroxide compound, a metal or ammonium halide and any resulting reaction products. It has been discovered that the preferred ternary ratio between the three added ingredients, the quaternary or protonizable nitrogen ammonium compound, the oxidant which is preferably a peroxide, and the halide source, e.g. metal or ammonium halides, respectively can range from 1:11 to 1:5:1 to 1:15:15. An optimal range is 1:3:1 to 1:3:3.

Use solutions are formed by combining, in an aqueous medium, the individual components consisting of a quaternary ammonium compound, a peroxygen compound and a metal halide. Reaction is virtually instantaneous, resulting in a use solution which can be used almost immediately. Alternately, the use solution can be formed by incorporating the pre-made complex into a solution. The use solution can be utilized in any application needing either antimicrobial or oxidizing efficacy.

The antimicrobial compositions of the invention are either solid-phase, powdered, gels, aerosols, non-aqueous liquids, or 2-part liquid mixtures which can be added to an aqueous rinse or wash liquid or a non-aqueous (e.g., mineral oil, lecithin) formulation.

The invention includes a process for preparing a solvent-free liquid, gel, aerosol, powder, or solid antimicrobial or antiviral complex including applying or generating heat, gaseous water vapor, or chemical hydrates, to a mixture of a solid, gel, or powder composition having a source of a quaternary or protonizable nitrogen compound; an oxidant; a halide source; and cooling the resulting complex to ambient temperature. In one embodiment, the mixture is heated in an extruder or hot-melt apparatus. Optionally, heat is applied or generated to a temperature above 30° C.

The invention further includes a process for preparing antimicrobial and antiviral compositions suitable for subsequent incorporation into solid, gel, aerosol, or non-aqueous liquid cleaning, sanitizing, or disinfecting products for treatment of surfaces. Thus, these include in powder, liquid, gel, or solid form: a) a source, preferably a natural one, of a quaternary or protonizable nitrogen compound; (b) an oxidant, preferably a peroxygen compound or oxidizing gas; (c) a halide or halogen source; and optionally (d) a source of acidity; wherein for each part by weight of the halide source there is about 0.1 to 30 parts by weight of the nitrogen compound, about 0.1 to 40 parts by weight of the oxidant compound, unless an oxidizing gas is use to form the complex in-situ and, then, an excess of the oxidant can be employed. The antimicrobial or antiviral composition is incorporated into the cleaning, disinfecting, or sanitizing substrate at a level of about 0.001 to about 95 weight %.

The invention also includes a process for making powder antimicrobial or antiviral compositions suitable for incorporation (casting, absorbing, adsorbing, spray-drying, etc.,) into solid, elastomeric, or fibrous substrates for residual antimicrobial or antiviral effects.

The invention also resides in a process for preparing antimicrobial or antiviral compositions comprising a combination of (a) a quaternary or protonizable nitrogen compound, preferably a natural source, with (b) a polyhalogen-containing anion, and (c) a water-soluble or dispersible substrate which greatly improves the solubility or efficacy of said complexes.

The antimicrobial solutions used in treating said surfaces typically have, for solid compositions, about 0.1 to 400 grams of antimicrobial composition per liter of water, preferably about 1 to 100 grams per liter, and most preferably about 2 to 30 grams per liter.

The two part liquid concentrate of the invention can also be used in the above situations. Preferably, the two part concentrate is mixed to provide a dilute aqueous solution of about 0.1 to 130,000 ppm of the total concentrate; wherein the surfaces are treated with the dilute aqueous solution.

The invention includes a number of antimicrobial and antiviral methods and processes. The invention can be found in a method of reducing microbial or viral populations on a surface or object; said method including treating said surface or object with an aqueous solution of an effective amount of a complex resulting from an in-situ reaction of a source of a quaternary or protonizable nitrogen compound, an oxidant, and a halide source. In one embodiment, the surface is a clean-in-place (CIP) system, while in another it is one of the many non-CIP surfaces encountered in preparing food (e.g., cutting boards, sinks, ware-wash systems, utensils, counter tops, transport belts, aseptic packaging, boot and hand-wash dip-pans, food storage facilities and anti-spoilage air circulation systems, food refrigeration and coolers, blanchers, food packaging materials, third-sink containers, etc.).

In yet another the surface is in a hospital, environment and are sanitized or disinfected surfaces in surgical, infirmity, birthing, mortuary, and clinical diagnosis, etc., rooms. These surfaces can be those typified as "hard surfaces" (such as walls, floors, bed-pans, etc.,), or woven and non-woven surfaces (such as surgical garments, draperies, bed linens, bandages, etc.,), or patient-care equipment (such as respirators, diagnostic equipment, shunts, body scopes, etc.,), or a plethora of surgical and diagnostic equipment. Also, the medical-related surfaces might be those of medical waste or blood spills. The microbes and viruses are often those which lead to tuberculosis, HIV, hepatitis', herpes', and other human pathogenic or opportunistic entities by physical contact or air transmission. The skin disease in question can be, for example, athletes foot fungus or hairy hoof wart disease. Alternatively, the disease can be a skin or transmittable viral disease such as parvovirus, coxsackie or herpes. The disease can also be a mycobacterial or bacterial type, such as tuberculosis or Legionella.

These compositions can also be used to reduce microbial and viral counts in air and liquids by incorporation into filtering media or breathing filters.

The invention also includes a method of reducing microbial or viral populations in a body or stream of water including treating said body or stream with an effective amount of a complex resulting from an in-situ reaction of a source of a quaternary or protonizable nitrogen compound, an oxidant, and a halide source. The body of water can be a swimming pool or a cooling tower, or can alternatively include food processing waters (e.g., flumes, can warmers, retort waters, third-sink sanitizing, bottle coolers, food sprays and misting systems, etc.,). beverage chillers and warmers, meat chilling or scalding waters, sanitizing gels, food processing antimicrobial garment sprays, and non-to-low-aqueous food preparation lubricants, oils, and rinse additives.

The complex resulting from an in-situ reaction of a source of a quaternary or protonizable nitrogen compound, an oxidant, and a halide source can also be used to reduce odors and microbial or viral populations in gaseous (especially air) streams by passing said aqueous streams through a bed, or woven or non-woven substrate or filter, including said complex. The complex can also be used for bleaching or reducing microbial or viral populations on woven or non-woven substrates, like linens or garments, by treating said substrate with an aqueous solution including the complex.

Skin diseases of—or on, or transmittable—mammals can also be treated with the same complex. Especially useful is the treatment of skin diseases on animals, or those which spread via transfer to air or surface substrates, such as diseases from fungi, bacteria and viruses. These spreadable skin diseases can include athletes foot fungus and hairy hoof wart disease, or one of the many organisms leading to Mastitis or other mammalian milking diseases. The disease can be a viral disease such as parvovirus, coxsackie virus, or herpes virus. The disease can also be bacterial, such as *S. aureus, E. coli, Streptococci*, etc., or a Mycobacterium type such as that leading to tuberculosis.

These compositions can also be used to reduce microbial and viral counts in air and liquids by incorporation into filtering media or breathing filters. Especially useful is for removal of water and air-born pathogens such as Legionella.

The same complex can be used in reducing microbes and odors in animal feeds and in animal watering stations, enclosures, in animal veterinarian clinics, animal inspection areas, animal surgical areas. Reductions in human pathogenic microbes on animals can be obtained by applying to said animals an aqueous solution, or non-aqueous solution or gel, of an effective amount of the complex. Finally, the complex can be used to reduce opportunistic pathogenic microbes on eggs, by applying to said eggs an aqueous solution of an effective amount of the complex; especially chicken eggs.

| Component | Useful Wt-% | Preferred Wt-% | More Preferred Wt-% |
|---|---|---|---|
| nitrogen source | 1–20 | 2–15 | 3–10 |
| oxidant compound | 1–40 | 3–20 | 4–10 |
| halide source | 1–40 | 1–15 | 2–10 |
| acidity source | 0–80 | 0–50 | 0–40 |
| wetting agents | 0–20 | 0–10 | 0–5 |
| inerts | 0–80 | 0–40 | 0–30 |

The present invention also includes as an alternative embodiment a two part liquid concentrate where each part contains an aqueous concentrate including a nitrogen source, an oxidant compound, preferably a peroxygen compound and optionally an acidity source in part (a) and a metal halide in part (b); and optionally, inerts and wetting agents.

Typical two part liquid formulation ranges are:

| Component | Useful Wt-% | Preferred Wt-% | More Preferred Wt-% |
|---|---|---|---|
| first part | | | |
| nitrogen source | 0.1–80 | 0.5–50 | 1–15 |
| oxidant compound | 0.1–75 | 1–35 | 10–20 |
| acidity source | 0–70 | 0–50 | 0–25 |
| wetting agents | 0–10 | 0.05–5 | 0.1–1 |
| inerts | 0–50 | 0–20 | 0–10 |
| water | balance | balance | balance |
| second part | | | |
| halide source | 0.1–80 | 0.5–30 | 1–15 |
| wetting agents | 0–10 | 0.05–5 | 0.1–1 |
| inerts | 0–50 | 0–20 | 0–10 |
| water | balance | balance | balance |

When used, a total actives concentration ranging from 10 to 100,000 ppm is preferred. Useful product use concentration ranges for sanitizing with either a liquid or solid composition are given in the table below:

| Component | Useful (ppm) | Preferred (ppm) | More Preferred (ppm) |
|---|---|---|---|
| nitrogen source | 1–10,000 | 10–5,000 | 20–1,000 |
| oxidant compound | 1–30,000 | 30–15,000 | 50–1,500 |
| acidity source | 0–20,000 | 0–5,000 | 0–1,000 |
| halide source | 1–30,000 | 10–15,000 | 20–1,500 |
| wetting agents | 0–5,000 | 0–500 | 0–100 |
| inerts | 0–50,000 | 0–10,000 | 0–1,000 |

Film forming

The composition of the invention may also contain one or more rheology modifiers, to enhance viscosity, or thicken and cause the aqueous treatment to cling to the surface being treated. Clinging enables the composition to remain in contact with the transient and resident pathogenic bacteria for longer periods of time, thereby promoting microbiological efficacy and resisting waste because of excessive dripping. The rheology modifier may be a film former or may act cooperatively with a film forming agent to form a barrier that provides additional protection.

Preferred rheology modifiers include colloidal aluminum silicate, colloidal clays, polyvinyl pyrrolidone, polyvinyl acetate, polyvinyl alcohol, polyalkylene oxides, polyacrylamides, or mixtures thereof.

Water soluble or water dispersible rheology modifiers that are useful can be classified as inorganic or organic. The organic thickeners can further be divided into natural synthetic polymers with the latter still further subdivided into synthetic natural-based synthetic petroleum-based.

Organic thickeners are generally compounds such as colloidal magnesium aluminum silicate (Veegum), colloidal clays (Bentonites), or silicas (Cab-O-Sils) which have been fumed to create particles with large surface size ratios.

Natural hydrogel thickeners of use are primarily vegetable derived exudates. For example, tragacanth, karaya, and acacia gums; and extractives such as caragheenan, locust bean gum, guar gum and pectin; or, pure culture fermentation products such as xanthan gum are all potentially useful in the invention. Chemically, all of these materials are slats of complex anionic polysaccharides. Synthetic natural-based thickeners having application are cellulosic derivatives wherein the free hydroxyl groups on the linear anhydro-glucose polymers have etherified or esterified to give a family of substances which dissolve in water and give viscous solutions. This group of materials includes the alkyl and hydroxyalkylcelluloses, specifically methylcellulose, hydroxyethylmethylcellulose, hydroxypropylmethylcellulose, hydroxybutylmethycellulose, hydroxyethylcellulose, ethylhydroxyethylcellulose, hydroxypropylcellulose, and carboxymethylcellulose. Synthetic petroleum-based water soluble polymers are prepared by direct polymerization of suitable monomers of which polyvinylpyrrolidone, polyvinylmethylether, polyacrylic acid and polymethacrylic acid, polyacrylamide, polyethylene oxide, and polyethyleneimine are representative.

All thickeners do not work with equal effectiveness in this invention. Preferred aqueous thickening agents are those which are extremely pseudoplastic (non-Newtonian, rapid relaxation), tend not to develop rigid three-dimensional structure from interpolymer interactions, have a low or negligible viscoelastic character and possess a high gel strength. Such rheological properties are manifested in a composition which has a smooth flowing appearance, is easy to pour and apply, coats uniformly without forming mussilage streamers as the applicator is withdrawn and remains firmly in place without significant sag. Examples of preferred rheology modifiers are xanthan gum and hydroxyalkylcelluloses.

Generally, the concentration of thickener used in the present invention will be dictated by the method of application. Spraying or misting requires a lower composition viscosity for easy and effective application of treatment than dipping. Film forming barrier dips typically require high apparent viscosity necessary to form thick coatings which insure improved prophylactic effect.

Additional film forming agents are included which typically work in conjunction with thickeners. In fact, many of the aforementioned rheology modifiers are themselves film formers of greater or lesser effectiveness; however, a preferred grade of polyvinyl alcohol when used with preferred thickeners such as xanthan gum or hydroxyalkylceluloses affords particularly useful properties to compositions of this teaching, most notably the development of "balanced" films which are sufficiently water-sensitive to be stripped off with conventional washing, but capably adherent to withstand premature loss of integrity between applications. The success of the barriers thus formed by compositions of this invention are, in part, a consequence of a hydrophobic-hydrophilic balance, caused when non-volatile ingredients, especially fatty acids, surfactants and hydrotropes, become resident throughout the film and whose individual properties become additive with those characteristics of the thickeners and film formers. Such inclusions also plasticize the film and render it pliable.

Polyvinyl alcohol is a polyhydroxide polymer having a polymethylene backbone with pendent hydroxy groups. The monomer does not exist, so the polyvinyl alcohol moiety is made by first forming polyvinyl acetate and removing acetate groups using a base catalyzed methanolysis. Polyvinyl acetate polymerization is accomplished by conventional processes and the degree of hydrolysis is controlled by preventing completion of the methanol reaction. Variation of film flexibility, water sensitivity, ease of salvation, viscosity, film strength and adhesion can be varied by adjusting molecular weight and degree of hydrolysis. The preferred polyvinyl alcohol for use in compositions herein has a degree of hydrolysis greater than 92%, preferably greater than 98%, most preferably greater than 98.5%; and, has a molecular weight that falls in the range of between about 15,000 and 100,000, but preferably between 40,000 and 70,000 corresponding to a solution viscosity (4% wt aqueous solution measured in centipoise (cP) at 20° C. by Hoeppler falling ball method) of 12–55 cP (0.012 to 0.055 Pa·s) and 12–25 cP (0.012 to 0.025 Pa·s)respectively.

Antimicrobial and Antiviral Treatment

Treatment of inanimate objects can be accomplished by spraying or wiping a use solution onto the object or surface. An object can also be treated via submersion into an adequate supply of the use solution, which is typically an aqueous solution containing a major proportion of water and an effective amount of an antimicrobial or antiviral complex. The use solution can also contain one or more film forming agents to prevent excessively rapid shedding of the treatment solution. Volumes of water, such as those found in swimming pools, water cooling towers and food process and transport streams, can be treated by addition of the complex (either made in-situ or pre-made via non-aqueous routes) to a concentrated liquid, gel, aerosol, solid, or powder to the water. Addition can take place within the main volume of water, or can occur within a makeup stream of fresh water being added to the main volume. Non-aqueous medium (such as oils or plastics) can be treated using an in-situ complex, or by incorporation of a pre-made complex.

It is believed that use solutions contain effective amounts of a poly-halogen complex which forms, in-situ, from the combination of a quaternary or protonizable nitrogen source, an oxidant and a halide source.

Additionally, microbial and viral control of gaseous (especially air) or liquid streams can be affected by the incorporation of effective amounts of a poly-halogen complex deposited onto a filtering substrate.

Microbial or viral populations on surfaces, objects, gaseous streams, and bodies of water can be reduced by applying thereto an effective amount of a complex of the formula

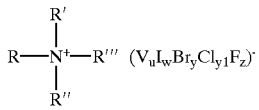

wherein R', R", R" and R'" are each independently a straight or branched, saturated or unsaturated, hydrocarbon group of 1 to 24 carbon atoms, in which the hydrocarbon group is unsubstituted or substituted by hydroxyl, carboxyl, or alkylamido, or in which the hydrocarbon group is uninterrupted or interrupted by a heteroatom; an aryl group, or aralkyl group in which alkyl has 1 to 4 carbon atoms; u is an integer from 0 to 1; w is an integer from 1 to 8; y and $y_1$ are each independently integers from 0 to 8; z is an integer from 0 to 1, and V is a non-halogen anion, except hydroperoxy, such as, for example, sulfate, methylsulfate, ethylsulfate, borate, phosphate, carbonate, silicate, tartrate, acetate, citrate, and the like. Preferably, y, $y_1$ and z can be 0.

Another useful complex is of the formula

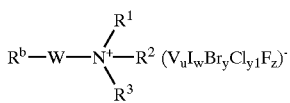

wherein W is a linear or branched alkylene, hydroxyalkylene or alkoxyalkylene group having 1–6 carbon atoms;

$R^b$ is $R^4$—CO—NH in which $R^4$ is a saturated or unsaturated, branched or linear hydrocarbon group having 4–22 carbon atoms, or $R^4$;

$R^1$ is hydrogen, A or $(A_n$—W—$CO_2^-M^+$ in which A is a linear or branched alkyl, hydroxyalkyl or alkoxyalkyl having 1–4 carbon atoms, n is an integer from 0 to 6, and $M^+$ is an alkali metal cation, a hydrogen ion or an ammonium cation;

$R^2$ is $(A)_n$—W—$CO_2^-M^+$;

$R^3$ is hydrogen or A; and V, u, w, y, $y_1$ and z are as previously defined.

Another effective complex is an acidified amine oxide of the formula

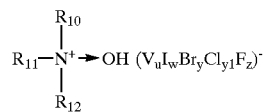

wherein $R_{10}$, $R_{11}$, and $R_{12}$ are each independently hydrogen, or at least one straight or branched alkyl group of 1 to 16 carbon atoms, in which alkyl is unsubstituted or substituted by hydroxyl, carboxyl, or alkylarnido, or in which alkyl is uninterrupted or interrupted by a heteroatom; an aryl group, or aralkyl group in which alkyl has 1 to 4 carbon atoms; and V, u, w, y, $y_1$ and z are as previously defined.

Yet another useful complex is of the formula

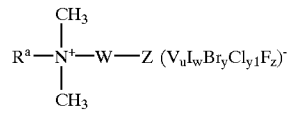

wherein Z is $CO_2H$, $SO_3H$, $OSO_3H$, or $OPO_3H$; W is a linear or branched alkylene, hydroxyalkylene or alkoxyalkylene group having 1–6 carbon atoms;

$R^a$ is a linear or branched alkyl, hydroxyalkyl or alkoxyalkyl group having 6–22 carbon atoms; or $R^4$—CO—NH(CH_2)_{x'}$ in which $R^4$ is a saturated or unsaturated, branched or linear alkyl group having 4–22 carbon atoms, and x' is an alkylene group having 1–6 carbon atoms; and V, u, w, y, $y_1$ and z are as previously defined.

Another useful complex is of the formula:

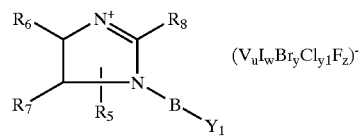

wherein $R_1$, $R_2$ and $R_3$ are each, independently, H or —$A_1$—Y in which $A_1$ is a $C_7$ to $C_{20}$ saturated or unsaturated, linear or branched alkylene group, and Y is H, $NH_2$, OH or $COOM_1$ in which $M_1$ is H or a Group I metal ion; B is a $C_1$ to $C_{20}$ saturated or unsaturated, linear or branched chain alkylene group, and $Y_1$ is H, $NH_2$, OH, $COOM_2$ or —NH—$COR_q$ in which $M_2$ is H or a Group I metal ion and $R_q$ is a $C_1$ to $C_{20}$ saturated or unsaturated, linear or branched chain alkyl group; $R_5$ is H or a $C_1$ to $C_3$ alkyl group at one of the nitrogen atoms; and V, u, w, y, $y_1$, and z are as previously defined.

Another useful complex is of the formula

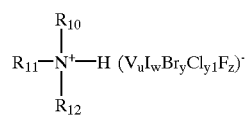

wherein $R_{10}$, $R_{11}$, and $R_{12}$ are each, independently, hydrogen or at least one straight or branched, saturated or unsaturated, hydrocarbon group of 1 to 24 carbon atoms, in which hydrocarbon is unsubstituted or substituted by hydroxyl, carboxyl, or alkylamido, or in which hydrocarbon chain is uninterrupted or interrupted by a heteroatom; an aryl group, or aralkyl group in which alkyl has 1 to 4 carbon atoms; and V, u, w, y, y, and z are as previously defined.

Another useful complex is of the formula $$R^a-\overset{R^b}{\underset{|}{N}H}-W-COOH \;\; (V_uI_wBr_yCl_{y1}F_z)^-$$

wherein $R^a$ is a linear or branched, saturated or unsaturated, alkyl, hydroxyalkyl or alkoxyalkyl group having 1–22 carbon atoms; $R^b$ is H or CH3; W is a linear or branched alkylene, hydroxyalkylene or alkoxyalkylene group having 1–4 carbon atoms, and V, u, w, y, $y_1$ and z are as previously defined.

Another useful complex is of the formula $$R^d-\overset{NH_3^+}{\underset{|}{C}H}-COOH \;\; (V_uI_wBr_yCl_{y1}F_z)^-$$

wherein $R^d$ is a common moiety as part of a natural amino acid; e.g., H, alkyl, hydroxyalkyl, thioalkyl, alkyl-aryl, carboxyl, amido, alkyl-amino, and the like, and V, u, w, y, $y_1$ and z are as previously defined.

Another useful complex is of the formula $$[\text{poly-peptide}]_{acidified}^{+} \; {}^{(V}{}_uI_wBr_yCl_{y1}F_z)^-$$

[poly-peptide]$_{acidified}^+$ refers to an acidified protein, and V, u, w, y, $y_1$, and z are as previously defined.

Skin Treatment

The invention also involves methods of treating skin diseases in, or on, mammals. If a short application is sufficient, a use solution can be sprayed or wiped onto an animal. Alternatively, the animal can be dunked into the use solution. If a longer residence time is required, the use solution can contain one or more film forming agents to slow down shedding of the treatment solution. If treating humans, the use solution can typically include a cream or lotion which can be applied to the skin and left in place. The antimicrobial or antiviral complexes described herein can be added to any suitable carrier, including hand lotions and the like. These same complexes and formulations can also be used to treat non-skin surfaces which might come in contact with the skin surfaces (e.g., bandages, gloves, breathing masks.

These methods include applying to the skin of said mammal an effective amount of a particular complex. One such useful complex is of the formula $$R-\overset{R'}{\underset{\underset{R''}{|}}{N^+}}-R''' \;\; (V_uI_wBr_yCl_{y1}F_z)^-$$

wherein R', R", R''' and R''', V, u, w, y, $y_1$ and z are as previously defined.

Another useful complex is of the formula $$R^b-W-\overset{R^1}{\underset{\underset{R^3}{|}}{N^+}}-R^2 \;\; (V_uI_wBr_yCl_{y1}F_z)^-$$

wherein W, $R^b$, $R^1$, $R^2$, V, u, w, y, $y_1$ and z are as previously defined.

Another effective complex for treating skin diseases of mammals is of the formula $$R_{11}-\overset{R_{10}}{\underset{\underset{R_{12}}{|}}{N^+}}\to OH \;\; (V_uI_wBr_yCl_{y1}F_z)^-$$

wherein $R_{10}$, $R_{11}$, and $R_{12}$, V, u, w, y, $y_1$ and z are as previously defined. In one embodiment, R' and R" are each methyl and R is a $C_8$–$C_{12}$ alkyl group. Alternatively, R', and R" are each methyl and R is a $C_8$–$C_{12}$ alkyl group.

Yet another effective complex is of the formula $$R^a-\overset{CH_3}{\underset{\underset{CH_3}{|}}{N^+}}-W-Z \;\; (V_uI_wBr_yCl_yF_z)^-$$

wherein Z, W, $R^a$, V, u, w, y, $y_1$ and z are as previously defined.

Another effective complex is of the formula $$\begin{array}{c} R_6 \diagdown \quad N^+ \quad \diagup R_8 \\ | \quad\quad | \\ R_7 \quad R_5 \quad B\diagdown Y_1 \end{array} \;\; (V_uI_wBr_yCl_{y1}F_z)^-$$

wherein:

$R_1$, $R_2$, $R_3$, B, $Y_1$, $R_q$, $R_5$, V, u, w, y, $y_1$, and z are as previously defined.

Another effective complex for treating skin diseases of mammals is of the formula $$R_{11}-\overset{R_{10}}{\underset{\underset{R_{12}}{|}}{N^+}}-H \;\; (V_uI_wBr_yCl_{y1}F_z)^-$$

wherein $R_{10}$, $R_{11}$, $R_{12}$, V, u, w, y, $y_1$, and z are as previously defined.

Especially useful complex is of the formula $$R^a-\overset{R^b}{\underset{|}{N}H}-W-COOH \;\; (V_uI_wBr_yCl_{y1}F_z)^-$$

wherein $R^a$, $R^b$, W, V, u, w, y, $y_1$, and z are as previously defined.

Likewise, another useful complex for treatment of skin is of the formula

wherein $R^d$, V, u, w, y, $y_1$, and z are as previously defined.

And another useful complex is of the formula

wherein [poly-peptide]$_{acidified}^+$, V, u, w, y, $y_1$, and z are as previously defined.

In the above complexes, a preferred embodiment is a complex where y, $y_1$, and z are 0.

The following examples further describe the present invention by way of illustration and are not meant to be limiting thereon.

EXAMPLE POWDERED FORMULATIONS

Formula I

| Compound | Wt-% |
| --- | --- |
| didecyl dimethyl ammonium chloride | 1.5 |
| sodium percarbonate (12.5% $H_2O_2$) | 25.0 |
| sodium bicarbonate | 24.0 |
| citric acid | 48.0 |
| potassium iodide | 1.5 |

Formula II

| Compound | Wt-% |
| --- | --- |
| alkyl dimethyl betaine | 10.0 |
| sodium percarbonate (12.5% $H_2O_2$) | 40.0 |
| sodium bicarbonate | 20.0 |
| sodium acid phosphate | 20.0 |
| cuprous iodide | 10.0 |

Formula III

| Compound | Wt-% |
| --- | --- |
| Miranol CEM-38 amphoteric | 1.5 |
| sodium percarbonate (12.5% $H_2O_2$) | 36.0 |
| citric acid | 10.0 |
| potassium iodide | 1.5 |

Formula IV

| Compound | Wt-% |
| --- | --- |
| Miranol CEM-38 amphoteric | 1.5 |
| sodium percarbonate (12.5% $H_2O_2$) | 36.0 |
| alpha olefin sulfonate | 10.0 |
| potassium iodide | 1.5 |

Formula V

| Compound | Wt-% |
| --- | --- |
| didecyl dimethyl ammonium chloride | 3.0 |
| sodium, dichloro isocyanuric acid | 20.0 |
| sodium metasilicate | 5.0 |
| sodium chloride | 58.0 |
| sodium bromide | 5.0 |
| sodium iodide | 9.0 |

Formula VI

| Compound | Wt-% |
| --- | --- |
| lecithin | 7.0 |
| sodium percarbonate (12.5% $H_2O_2$) | 50.0 |
| sodium chloride | 30.0 |
| potassium iodide | 6.0 |
| magnesium sulfate | 7.0 |

Formula VII

| Compound | Wt-% |
| --- | --- |
| didecyl dimethyl ammonium chloride | 3.0 |
| sodium perborate | 40.0 |
| sodium chloride | 30.0 |
| sodium bisulfate | 20.0 |
| sodium bromide | 1.0 |
| sodium iodide | 6.0 |

Formula VIII

| Compound | Wt-% |
| --- | --- |
| milk protein | 1.0 |
| sodium percarbonate (10.0% $H_2O_2$) | 35.0 |
| citric acid | 40.0 |
| sodium chloride | 21.0 |
| cuprous iodide | 3.0 |

Formula IX

| Compound | Wt-% |
| --- | --- |
| cetyl trimethyl ammonium chloride | 1.5 |
| sodium percarbonate (12.5% $H_2O_2$) | 36.0 |
| alpha olefin sulfonate | 10.0 |
| potassium iodide | 1.5 |

Examples of Two-Part Liquid Compositions:

| Formula # | First Part Component | Wt-% | Second Part Component | Wt-% |
|---|---|---|---|---|
| X | lauramine oxide | 3.0 | hydrogen peroxide | 5.0 |
| | potassium iodide | 0.9 | water | balance |
| | sodium, lauryl sulfate | 14.0 | | |
| | HCl | to pH = 6 | | |
| | water | balance | | |
| XI | lecithin | 2.0 | potassium iodide | 2.0 |
| | hydrogen peroxide | 6.0 | water | balance |
| | citric acid | to pH = 3.0 | | |
| | water | balance | | |
| XII | didecyl dimethyl ammonium chloride | 2.0 | potassium iodide | 10.0 |
| | hydrogen peroxide | 15.0 | water | balance |
| | citric acid | to pH < 8 | | |
| | water | balance | | |
| XIII | didecyl dimethyl ammonium chloride | 0.1 | potassium iodide | 1.0 |
| | peracetic acid | 0.8 | water | balance |
| | hydrogen peroxide | 4.1 | | |
| | water | balance | | |
| XIV | didecyl dimethyl ammonium chloride | 0.1 | potassium iodide | 1.0 |
| | peracetic/peroctanoic acids | 0.8 | water | balance |
| | hydrogen peroxide | 4.1 | | |
| | water | balance | | |
| XV | nonylphenol ethoxylate (9.5 EO) | 10.0 | hydrogen peroxide | 5.0 |
| | potassium iodide | 0.1 | water | balance |
| | Monateric CEM | 1.0 | | |
| | citric acid | to pH = 4 | | |
| | water | balance | | |
| XVI | C8 dimethyl amine oxide | 10.0 | sodium iodide | 10.0 |
| | hydrogen peroxide | 30.0 | water | balance |
| | optional acid | to pH < 8 | | |
| | water | balance | | |
| XVII | didecyl dimethyl ammonium chloride | 10.0 | potassium iodide | 20.0 |
| | hydrogen peroxide | 20.0 | water | balance |
| | water | balance | | |
| XVIII | sodium lauryl sulfate | 18.0 | hydrogen peroxide | 5.0 |
| | potassium iodide | 0.2 | nonylphenol ethoxytate | 1.0 |
| | Monaquat PTC | 1.0 | water | balance |
| | citric acid | to pH = 6 | | |
| | water | balance | | |

EXAMPLE OF SOLID BLOCK COMPOSITIONS

Solid Block Formula XIX

| Compound | Wt-% |
|---|---|
| choline chloride | 1.5 |
| sodium percarbonate (12.5% $H_2O_2$) | 25.0 |
| sodium bicarbonate | 24.0 |
| citric acid | 48.0 |
| potassium iodide | 1.5 |

Solid Block Formula XX

| Compound | Wt-% |
|---|---|
| choline chloride | 1.6 |
| sodium percarbonate (12.5% $H_2O_2$) | 4.5 |

-continued

Solid Block Formula XX

| Compound | Wt-% |
|---|---|
| citric acid | 62.5 |
| dipotassium hydrogen phosphate | 30.8 |
| potassium iodide | 0.6 |

EXAMPLE OF NON-AQUEOUS LIQUID COMPOSITIONS

Non-Aqueous Liquid Formula XXI

| Compound | Wt-% |
|---|---|
| lecithin | 23.8 |
| mineral oil | 71.4 |
| iodine | 4.8 |

Non-Aqueous Liquid Formula XXII

| Compound | Wt (g) |
| --- | --- |
| choline chloride | 50.2 |
| iodine | 91.3 |

Non-Aqueous Liquid Formula XXIII

| Compound | Wt (g) |
| --- | --- |
| choline chloride | 100.0 |
| iodine | 181.6 |

ADDITIONAL EXAMPLES OF PROTONIZABLE OR ACIDIFIED POWDER COMPOSITIONS

Formula XXIV

| Compound | Wt-% |
| --- | --- |
| taurine | 3.0 |
| sodium percarbonate (12.5% $H_2O_2$) | 40.0 |
| sodium diacetate | 40.0 |
| sodium acid phosphate | 15.0 |
| potassium iodide | 2.0 |

Formula XXV

| Compound | Wt-% |
| --- | --- |
| choline chloride | 1.3 |
| sodium percarbonate (12.5% $H_2O_2$) | 18.8 |
| sodium diacetate | 38.6 |

Formula XXV

| Compound | Wt-% |
| --- | --- |
| citric acid | 38.6 |
| potassium iodide | 2.7 |

Formula XXVI

| Compound | Wt-% |
| --- | --- |
| milk protein | 1.0 |
| sodium percarbonate (10.0% $H_2O_2$) | 35.0 |
| citric acid | 40.0 |
| sodium chloride | 21.0 |
| cuprous iodide | 3.0 |

Formula XXVII

| Compound | Wt-% |
| --- | --- |
| choline chloride | 1.5 |
| sodium percarbonate (12.5% $H_2O_2$) | 25.0 |
| sodium bicarbonate | 24.0 |
| citric acid | 48.0 |
| potassium iodide | 1.5 |

Working Example #1

We have discovered that certain attributes can be used as evidence of in situ antimicrobial and antiviral compositions of the present invention. These attributes include color, pH, UV absorption and oxidation reduction potential, or ORP. Table 1 shows the results of mixing certain near-neutral ternary or quaternary combinations of quaternary ammonium compounds plus halogen salts plus hydrogen peroxide.

TABLE 1

| | Composition | QUAT:H2O2:KX[1] (wt ratio) | Resultant pH | Resultant Color | UV-VIS[2] Maximum |
| --- | --- | --- | --- | --- | --- |
| Single Component Controls | | | | | |
| 1 | didecyl dimethyl ammonium chloride | 1:0:0 | 7.0 | uncolored | none |
| 2 | cetyl trimethyl ammonium chloride | 1:0:0 | 7.2 | uncolored | none |
| 3 | cocoa dimethyl amine oxide | 1:0:0 | 5.9 | uncolored | none |
| 4 | cetyl dimethyl piperidinium chloride | 1:0:0 | 6.8 | uncolored | none |
| 5 | coconut hydroxy ethyl imidazoline | 1:0:0 | 6.2[5] | uncolored | none |
| 6 | cocamidopropyl hydroxy sultaine | 1:0:0 | 5.9[5] | uncolored | none |
| 7 | sodium, cocoa ampho dipropionate[3] | 1:0:0 | 5.5 | uncolored | none |
| 8 | $H_2O_2$ | 0:1:0 | 5.6 | uncolored | |

TABLE 1-continued

| Composition | QUAT:H2O2:KX[1] (wt ratio) | Resultant pH | Resultant Color | UV-VIS[2] Maximum |
|---|---|---|---|---|
| 9 KX = KI | 0:0:1 | 6.2 | uncolored | |
| 10 KX = KBr | 0:0:1 | 6.5 | uncolored | |
| Dual Component Controls | | | | |
| 11 didecyl dimethyl ammonium chloride: $H_2O_2$ | 1:1:0 | 6.7 | uncolored | none |
| | 1:3:0 | 5.8 | | none |
| | 3:1:0 | 6.4 | uncolored | none |
| | 1:1:0 | adjusted to 9.6[4] | uncolored uncolored | none |
| 12 cetyl dimethyl piperidinium chloride: $H_2O_2$ | 1:3:0 | 6.8 | uncolored | none |
| | 1:6:0 | 6.1 | uncolored | none |
| 13 $H_2O_2$:KI | 0:1:1 | 7.6 | faint yellow | 295 nm |
| | 0:1:3 | 7.4 | faint yellow | 295 nm |
| | 0:3:1 | 6.9 | faint yellow | 295 nm |
| 14 didecyl dimethyl ammonium chloride: KI | 1:0:1 | 7.0 | uncolored | none |
| | 3:0:1 | 6.6 | uncolored | none |
| | 1:0:3 | 6.7 | uncolored | none |
| 15 cocoa dimethyl amine oxide: KI | 3:0:1 | 6.1 | uncolored | none |
| | 1:0:6 | 6.7 | uncolored | none |
| Ternary Compositions | | | | |
| 16 didecyl dimethyl ammonium chloride:$H_2O_2$:KI | 1:1:1 | 8.9 | bright yellow | 295 + 365 nm |
| | 1:1:2 | 9.2 | | |
| | 1:2:1 | 8.9 | bright yellow | 295 + 365 nm |
| | 2:1:1 | 8.8 | | |
| | 1:1:6 | 9.3 | bright yellow | 295 + 365 nm |
| | 1:6:1 | 8.6 | | |
| | 6:1:1 | 8.3 | bright yellow | 295 + 365 nm |
| | 1:3:1 | adjusted to 10.2[4] | bright yellow bright yellow bright yellow colorless | 295 + 365 nm 295 + 365 nm 295 + 365 nm 288 nm |
| 17 cetyl dimethyl piperdinium chloride:$H_2O_2$:KI | 1:1:1 | 8.3 | bright yellow | 295 + 365 nm |
| | 1:1:3 | 8.4 | bright yellow | 295 + 365 nm |
| 18 cocoa dimethy amine oxide:$H_2O_2$:KI | 1:3:1 | — | bright yellow | 295 + 365 nm |
| 19 cocoa dimethyl betaine:$H_2O_2$:KI | 1:3:1 | 7.6 | bright yellow | 295 + 365 nm |
| 20 coconut hydroxy ethyl imidazoline | 1:3:1 | adjusted to 6.2[5] | bright yellow | 295 + 365 nm |
| 21 cocamidopropyl hydroxy sultaine | 1:3:1 | adjusted to 5.9[5] | bright yellow | 295 + 365 nm |
| Mixed Halogen Compositions | | | | |
| 22 didecyl dimethyl ammonium chloride:$H_2O_2$KI: KBr | 1:1:0:1 | 6.5 | uncolored | none |
| 21 didecyl dimethyl ammonium chloride:$H_2O_2$KI: KBr | 1:1:1:1 | 9.1 | bright yellow | 295 + 365 nm |

[1]KX = potassium iodide and/or potassium bromide
[2]UV-VIS = ultra violet to visible spectral absorbances from 230–700 nm.
[3]Adjusted in pH using citric acid.
[4]As per U.S. Pat. No. 5,620,527 and 4,941,989; pH adjusted upward with NaOH.
[5]Acidified with HCl to the desired pH.

Table 1 shows that ternary mixtures result in pH values substantially higher than the pH values of any of the individual components. For example, a 1:1:1 wt-% of the quaternary component hydrogen peroxide and potassium iodide as seen in Sample 14 results in a pH of 8.9, while none of the individual components have a pH greater than 7. Note also the bright yellow color formed in all the ternary nitrogen compositions containing a quaternary nitrogen, an oxidant, and an iodide (e.g., experiments 14–17 and 19) Conversely, none of the single or binary combinations yield the colored in-situ composition. It will be demonstrated later that these compositions possess strong antimicrobial activity. The yellow color is an indication of the antimicrobial activity of the composition. It is also noteworthy that the yellowish color formation is evidenced by the UV-visible absorbance at 365 nm; and is in obvious contrast to no absorbance or the free iodide absorbance at 295 nm; demonstrating the unique in-situ complex.

Table 1 also demonstrates the uniqueness of the present invention over that taught by Kramer et al., in U.S. Pat. Nos. 4,941,989 and 5,620,527, which teach the use of antimicrobial compositions made of alkaline per-salts of quaternary ammonium compounds and hydroperoxide anions at pH's of greater than 9.5. The last entries of experiments 9 and 14 of Table 1 (i.e., quat plus peroxide, with and without iodide) demonstrate that the active complex of the invention is distinctive from the aforementioned prior art by the lack of formation of the yellow colored complex and the indicative ultraviolet absorbency.

We also discovered that the compositions appear to require the presence of iodine to impart the synergistic properties discovered in the invention. This can be seen by comparing examples 18 and 19. While there is a significant difference in pH between these two, the only difference is the lack of iodine in composition 18.

Although not shown on this table, a maximum pH was generated using a 1.6:2.1:1.3 wt-% in the aforementioned components. A ternary or higher combination of these compositions results in an acceptable low limit of pH>7.1, a preferred value of >8.0 and a most preferred value >8.5.

Working Example #2

Table 2 shows similar color formation and UV-VIS results to Table 1 using a variety of permanent or protonizable quaternary entities. Again, the evidence of the yellowish color and UV-VIS absorptions are found using the compositions of the present invention; in contrast to the control or prior art compositions.

TABLE 2

| Composition | Nitrogen[1]:<br>$H_2O_2$:KI:acid<br>(wt:wt:wt:wt) | Composition Color | UV VIS Maximum |
|---|---|---|---|
| Controls | | | |
| 1  Phosphoteric PTC[2]:KI | 1:0:1:0.4 | colorless | none |
| choline chloride:KI | 1:0:1:0 | colorless | none |
| MONA AT-1200[2] | 1:0:1:1 | colorless | none |
| lecithin:$H_2O_2$ | 1:0:1:0.2 | colorless | none |
| protein-1[3]:KI | 1:0:1:0.2 | colorless | none |
| ADBAC QUAT[4]:KI | 1:0:1:0 | colorless | none |
| protein-2[5]:KI | 1:0:1:0.2 | colorless | none |
| KI | 0:0:1:0.2 | light yellow | trace 295 nm only |
| $H_2O_2$ | 0:1:0:0.2 | colorless | none |
| POAA[6] | 0:1:0:1.5 | colorless | none |
| $H_2O_2$/OA/POAA[7] | 0:1:0:1.0 | colorless | none |
| QUAT monohalide[10] | 1:0:1:0.2 | colorless | none |
| QUAT[4]:POAA[6] | 0.2:1:0:0.5 | colorless | none |
| QUAT:$H_2O_2$(Ultra-Kleen HW)[8] | unknown | colorless | none |
| QUAT:$H_2O_2$(Ultra Kleen liquid)[9] | 0.2:0.7:0:0 | | |
| Various Nitrogen Compositions[1] | | | |
| 2  Phosphoteric PTC[2] | 1:1:1:1 | bright yellow | 365 nm, low 295 nm |
| choline chloride | 1:1:1:0.2 | bright yellow | 365 nm, low .295 nm |
| lecithin | 1:1:1:0.2 | yellow | equal 365 + 295 nm |
| protein | 1:1:1:0.2 | bright yellow | equal 365 + 295 nm |
| sarcosine | 1:1:1:0.2 | bright yellow | 365 nm, low 295 nm |
| glycine | 1:1:1:0.2 | bright yellow | 365 nm, low 295 nm |
| protein[4] | 1:1:1:0.2 | bright yellow | 365 nm, low 295 nm |
| QUAT monohalide[10] | 1:1:1:0.2 | bright yellow | 365 nm, low 295 nm |

[1]Nitrogen = quaternary or protonizable nitrogen; sometimes using citric acid for quaternizing non-permanent sources.
[2]Mona Industries Inc.
[3]Protein source from vegetable mix.
[4]Alkyl (mixed) dimethyl benzyl ammonium chloride.
[5]Protein source from blood.
[6]POAA = peroxyacetic acid blend; Ecolab Inc., St. Paul, MN
[7]U.S. Pat. No. 5,200,189; $H_2O_2$/OA/POAA = hydrogen peroxide/octanoic/peroxyacetic acid blend; Ecolab Inc., St. Paul, MN
[8]U.S. Pat. No. 5,620,527, U.S. Pat. No. 4,941,989; Ultra-Kleen HW; The Sterilex Corp.; Owings Mills, MD
[9]U.S. Pat. No. 5,620,527, U.S. Pat. No. 4,941,989; Ultra-Kleen Liquid; The Steritex Corp.; Owings Mills, MD
[10]Didecyl dimethyl ammonium chloride.

Working Example #3

Table 3 shows results of the testing done to demonstrate the antimicrobial efficacy combinations of the invention towards the reduction of molds. An aqueous suspension of the mold spore *Penicillium expansum* (ATCC 7861), was exposed to the test compositions for various lengths of time. The antimicrobial was neutralized and an aliquot inoculated onto Sabouraud Dextrose agar, followed by incubation for five days at 26° C.

TABLE 3

| Test | QUAT[1]:H2O2:KI (wt:wt:wt) total = 500 ppm[2] | pH | Color | Microbial Reduction[3] of *Penicillium expansum* (time required for > 4.6 log reduction) |
|---|---|---|---|---|
| Single Component Controls | | | | |
| 1 | 1:0:0 | 7.0 | none | 2 hours |
| 2 | 0:1:0 | 5.6 | none | no reduction at any time |
| 3 | 0:0:1 | 6.2 | none | no reduction at any time |
| Binary Component Controls | | | | |
| 4 | 1:1:0 | 6.7 | none | 2 hours |
| 5 | 0:1:1 | 7.6 | faint yellow | 2 hours |
| 6 | 1:0:1 | 7.0 | none | >2 hours |
| Ternary Component Examples | | | | |
| 7 | 3:1:1 | 8.7 | bright yellow | <15 minutes |
| 8 | 1:3:1 | 9.0 | bright yellow | <15 minutes |
| 9 | 1:1:3 | 9.1 | bright yellow | <15 minutes |

[1]QUAT = cetyl trimethyl ammonium chloride
[2]The total actives equals the ppm's of QUAT + $H_2O_2$ + KI.
[3]Microbial reduction relative to an untreated control at $4.2 \times 10^5$ cfu/ml.

The test results clearly show the effectiveness, against a mold, of the ternary positions in comparison to either the single or binary compositions. We note that the hydrogen peroxide alone and the potassium iodine alone, as shown in examples 2 and 3, to have any antimicrobial activity; and the QUAT (cetyl trimethyl ammonium chloride) itself, or in any binary mixture, is extremely slow in affecting microbial reduction (tests 1–6). Conversely, for the inventive tests of 7–9, the rate of mold kill is increased by over 8-times by the in-situ compositions of the invention; i.e., all three ternary compositions of the are found to decrease the mold-kill time from two hours, or greater, to less than fifteen minutes.

We note that the pH in color observations as shown in Table 1, namely the higher pH and bright yellow color of the ternary compositions, is seen here only in the antimicrobially effective, or enhanced, compositions. This indicates that in the compositions of the invention, color and pH are effective indicators of antimicrobial activity, and correlate to disinfecting and sanitizing performance.

Working Example #4

Table 4 is similar to Table 4 in that it demonstrates the synergism of the in situ generated ternary compositions against a mold. The test procedure is identical to that in the previous working example.

TABLE 4

| Test Experiment | QUAT[1]:H2O2:KI (wt:wt:wt) | Active[2] QUAT Level (ppm) | Solution Color | Microbial Log Reduction[3] |
|---|---|---|---|---|
| Single Component Controls | | | | |
| 1 QUAT[c] | 1:0:0 | 500 | none | 4.0 |
| 2 $H_2O_2$ | 0:1:0 | 0 | none | 0 |
| 3 KI | 0:0:1 | 0 | none | 0 |
| Ternary Component Examples | | | | |
| 4 QUAT:$H_2O_2$:KI | 3:1:1 | 300 | bright yellow | >4.6 |
| 5 QUAT:$H_2O_2$:KI | 1:3:1 | 100 | bright yellow | >4.6 |
| 6 QUAT:$H_2O_2$:KI | 1:1:3 | 100 | bright yellow | >4.6 |
| 7 QUAT:$H_2O_2$:KI | 1:1:1 | 50 | bright yellow | 4.5 |

[1]QUAT = cetyl trimethyl ammonium chloride.
[2]The active QUAT level is the weight percent of the trimethyl ammonium chloride.
[3]Microbial log reduction of the mold *Penicillium expansum* relative to an untreated control at $1.5 \times 10^6$ cfu/ml; using a 15-minute exposure time.

Again, the results demonstrate the effectiveness of the ternary compositions versus single-component compositions towards a mold. We note the color observations do correlate with the microbial reduction levels. Also, the results demonstrate the enhanced efficacy of the current compositions in being able to induce substantial microbial control while reducing the total active level of active nitrogen-based quaternary ammonium compounds; especially compare the conventional composition of test 1 versus the invention shown in the compositions of tests 6 or 7 (a 5–10× reduction in QUAT).

Working Example #5

Table 5 demonstrates the chemical uniqueness of the present invention compared to known embodiments with regards to UV absorbance. The results verify the different chemical moieties present. The free iodine at 295 nm is evidenced in many of the samples, but the distinctive differentiating absorbances are also indicated. The invention is conclusively evidenced by the absorbance maximum at 365 nm.

TABLE 5

| Composition | Actives | UV max |
|---|---|---|
| Prior Art | | |
| 1 Divosan MH[a] | interhalogens | 295 nm and 305 nm |
| 2 Ultra Kleen ™ Liquid[e] U.S. Pat. No. 5,620,527 and U.S. Pat. No. 4,941,989 | quat hydroperoxide[e] | 283 nm |
| 3 U.S. Pat. No. 5,620,527 and U.S. Pat. No. 4,941,989 | iodized quat hydroperoxide[f] | none |
| 4 U.S. Pat. No. 5,620,527 and U.S. Pat. No. 4,941,989 | iodized quat hydroperoxide[6] | mainly 288 nm |
| 5 Ultra Kleen ™ HW Powder[e] U.S. Pat. No. 5,620,527 and U.S. Pat. No. 4,941,989 | quat hydroperoxide[e] | 278 nm |
| 6 Mikroklene[i] | $I_2$ | 295 nm |
| 7 WO 94/00548 | quats/peracids | none |
| 8 Oxy Brite[j] | $H_2O_2$ | none |
| 9 Ster Bac Blue[h] | QUAT monochloride | 235 nm |
| 10 didecyl dimethyl ammonium chloride | QUAT monochloride | none |
| Present Invention | | |
| 9 1[b] | QUAT-1 complex | mainly 365 nm |
| 10 2[c] | QUAT-2 complex | mainly 365 nm |
| 11 3[d] | Betaine complex | 295 nm and 365 nm |

[a]Divosan MH is described in U.S. Pat. Nos. 4,822,513; 5,047,164; and 5,202,047.
[b]1 is composition 17 from Table 1.
[c]2 is composition 4 from Table 4.

TABLE 5-continued

| Composition | Actives | UV max |
|---|---|---| d)3 is composition 15 from Table 1.
e)As per U.S. Pat. Nos. 5,620,527 and 4,941,989; The Sterilex Corporation; Owings Mills, MD.
f)As per U.S. Pat. Nos. 5,620,527 and 4,941,989 using choline chloride and with iodide added.
g)As per U.S. Pat. Nos. 5,620,527 and 4,941,989 using ADBAC quats with iodide added.
h)A quaternary ammonium chloride blend; Ecolab Inc., St. Paul, MN
i)An iodine sanitizer; Ecolab Inc., St. Paul, MN
j)A peroxide product; Ecolab Inc., St. Paul, MN Working Example #6

Table 6 demonstrate various 2 part liquid formulations according to the invention. A variety of nitrogen sources are utilized. Results recorded include the color of the solution and the microbial log reduction of gram-positive and gram-negative bacteria (*E. coli* and *S. aureus*, respectively). As shown earlier there is a direct correlation between color of the solution and microbial efficacy. In this we are defining a lack of microbial efficacy to be less than a 0.5 log reduction, while effectiveness is being defined as greater a than 1.0 log reduction. Looking at Table 6, there is an obvious direct correlation between color and antimicrobial activity.

TABLE 6

| Composition | Nitrogen[1]:$H_2O_2$:KI (wt:wt:wt) | Composition Color | Log Reduction[2] E. coli | S. aureus |
|---|---|---|---|---|
| | Single Component Controls[3] | | | |
| 1 | cocoa dimethyl betaine | 1:0:0 | colorless | 0 | 0 |
| 2 | C8 amine oxide[4] | 1:0:0 | colorless | 0 | 0 |
| 3 | cocodimethyl betaine | 1:0:0 | colorless | 0 | 0 |
| 4 | alkyl sultaine[5] | 1:0:0 | colorless | 0 | 0 |
| 5 | choline chloride | 1:0:0 | colorless | 0 | 0 |
| 6 | lecithin | 1:0:0 | colorless | 0 | 0 |
| 7 | $H_2O_2$ | 0:1:0 | colorless | 0.2 | 0 |
| 8 | KI | 0:0:1 | colorless | 0 | 0 |
| | Ternary Compositions | | | | |
| 9 | betaine[6]:$H_2O_2$:KI | 1:3:1 | yellow | 4.0 | 2.7 |
| | amine oxide[7]:$H_2O_2$:KI | 1:3:1 | bright yellow | 3.6 | 2.9 |
| | alkyl sultaine[5]:$H_2O_2$:KI | 1:3:1 | bright yellow | 4.5 | 3.8 |
| | imidazoline[8]:$H_2O_2$:KI | 1:3:1 | yellow | >5.0 | 0.0 |
| | choline:$H_2O_2$:KI (pH = 3) | 1:3:1 | bright yellow | >5.2 | >4.7 |
| | choline:$H_2O_2$:KI (pH = 5) | 1:3:1 | bright yellow | >5.2 | >4.7 |
| | lecithin:$H_2O_2$:KI (pH = 3) | 1:3:1 | bright yellow | >5.2 | >4.7 |
| | lecithin:$H_2O_2$:KI (pH = 5) | 1:3:1 | bright yellow | 4.9 | 0.1 |
| | lecithin:$H_2O_2$:KI (pH = 9) | 1:3:1 | colorless | 0.0 | 0.0 |

[1]Nitrogen quaternary or protonizable nitrogen.
[2]Log Reduction vs. an untreated control, 30 second contact time; with a reduction of >1.0 units demonstrating effectiveness.
[3]Not counting acid for pH adjustment.
[4]Octyl dimethyl aznine oxide
[5]Mirataine CBS from Rhone-Poulenc.
[6]Same betaine as experiment 1.
[7]Same betaine as experiment 2.
[8]Monastat 1195 from Mona Industries.

Working Example #7

Table 7 compares formulas of the present invention with prior art examples for the reduction of gram-positive and gram-negative bacteria. The results demonstrate these compositions to be comparable, or better, in microbial efficacy to those of the prior art, while utilizing lower levels of total actives (from 2–8 times lower in actives concentrations).

TABLE 7

| | Product Name | Composition Actives | Actives Conc. (ppm)[1] | Log Reduction (CFU/ml)[2] S. aureus | E. coli |
|---|---|---|---|---|---|
| | Prior Art | | | | |
| 1 | Hydrogen Peroxide | $H_2O_2$ | 300 | 0.4 | 0.2 |
| 2 | Vortexx[3] | $H_2O_2$/OA/POAA | 95 | 5.4 | 3.1 |
| 3 | Ster-Bac Blue[4] | QUAT | 98 | 5.8 | 0.8 |
| 4 | Ultra-Kleen ™ Liquid[5] | QUAT/$H_2O_2$ | 781 | 5.4 | 3.1 |
| 5 | Virucidal Extra[6] | unknown | 1:400[7] | 1.2 | 0.3 |
| | Present Invention | | | | |
| 6 | powder Formula VI | $H_2O_2$/QUAT/KI | 50[8] | >6.0 | >5.2 |
| 7 | Mixture 2[9] | $H_2O_2$/QUAT/KI[9] | 50[8] | >6.0 | >5.2 |

[1]Active Concentrations based on use recommendations from supplier labels.
[2]30 second exposure reductions of *E. coli* ATCC 11229.
[3]A synergistic blend of hydrogen peroxide/octanoic/peroxyacetic acid blend; Ecolab Inc., St. Paul, MN
[4]A quaternary ammonium chloride blend; Ecolab Inc., St. Paul, MN
[5]A quaternary hydroperoxide blend; The Sterilex Corp.; Owings Mills, MD; U.S. Pat. Nos. 5,620,527 and 4,941,989.
[6]A broad spectrum virucide, bactericide, fungicide; AVS (N.I.); Newtownards, CO. DOWN; G.B. 9406046-2.
[7]The actives levels are unknown so the use dilution is listed.
[8]Based on $I_2$ conversion equivalency.
[9]The choline chloride composition of experiment 2, Table 2.

Working Example #8

Table 8 demonstrates virucidal efficacy of the compositions of the present invention; and compares these results with four commercial virucidal products. The results demonstrate the substantial virucidal efficacy, as defined by the difference between the virus titer and the virucidal test being greater than $10^3$, for use against *Canine parvovirus* and other human or animal viral agents and pathogens; especially those of naked-DNA or naked-RNA types.

TABLE 8

| | Product Name | Actives Conc. (ppm)[1] | Canine parvovirus ATCC VR-935 Virucidal Result $ID_{50}$[2] | Virucidal Efficacy (>$10^3$ required)[3] |
|---|---|---|---|---|
| | Prior Art | | | |
| 1 | Vortexx[4] | 380 | $10^{2.5}$ | $10^2$ |
| 2 | Ultra-Kleen ™ Liquid[5] | 6250 | $10^{3.5}$ | $10^1$ |
| 3 | Virucidal Extra[6] | 1:100[8] | $10^{2.5}$ | $10^2$ |
| 4 | Virkon S[7] Present Invention | 1:100[8] | $10^{2.5}$ | $10^2$ |
| 5 | liquid Formula XVII | 450[9] | $10^{1.5}$ | $10^5$ |

TABLE 8-continued

| Product Name | Actives Conc. (ppm)[1] | Canine parvovirus ATCC VR-935 Virucidal Result $ID_{50}$[2] | Virucidal Efficacy ($>10^3$ required)[3] |
|---|---|---|---|
| 6 liquid Formula XVII | 200[9] | $10^{1.5}$ | $10^5$ |
| 7 liquid Formula XVII | 100[9] | $10^{1.5}$ | $10^5$ |
| 8 Solid Formula XIX | 60[9] | $10^{4.7}$ | $<10^2$ |
| 9 Solid Formula XIX | 120[9] | $10^{2.5}$ | $10^4$ |
| 10 Solid Formula XIX | 240[9] | $10^{2.5}$ | $10^4$ |

[1]Active Concentrations based on rise recommendations from supplier labels.
[2]10 minute exposure time; $ID_{50}$ calculated according to the Reed-Muench equation.
[3]The difference between the virus titer control and the virucidal test result; $>10^3$ needed for virucidal efficacy.
[4]A synergistic blend of hydrogen peroxide/octanoic/peroxyacetic acid blend; Ecolab Inc., St. Paul, MN
[5]A quaternary hydroperoxide blend; The Sterilex Corp.; Owings Mills, MD; U.S. Pat. Nos. 5,620,527 and 4,941,989
[6]A broad spectrum virucide, bactericide, fungicide; AVS (N.I.); Newtownards, CO. DOWN; G.B. 9406046-2.
[7]A broad spectrum virucide, bactericide, fungicide; Antec International; Sudbury, Suffolk, England; GB 2164851.
[8]The actives levels are unknown so the use dilution is listed.

Working Example #9

Table 9 compares the virucidal efficacy of the composition of the present invention, toward parvoviruses in general, with published results against Feline parvovirus. The results indicate a 10–40× reduction in actives to produce kill versus the published prior art.

TABLE 9

| Viral Agent | Minimum Concentration (for 10-minute inactivation)[1] |
|---|---|
| NaOCl | 2,000 ppm |
| IPA | 500,000 ppm |
| Ethanol | 500,000 ppm |
| Benzyl Quats | 5,000 ppm |
| A33 Dry[2] | 1,800 ppm (failed) |
| Iodophor (as $I_2$) | 5,000 ppm (1-log) |
| o-phenylphenol G | 100,000 ppm |
| Glutaraldehyde | 10,000 (2-log) |
| Solid Formula XIX | 600 ppm product (120 ppm actives) |
| Liquid Formula XVII | 500 ppm product (100 ppm actives) |

[1]"Disinfection, Sterilization, and Preservation" Lea & Febiger; Philadelphia, PA; 1991 p.413.
[2]Quaternary ammonium compounds; Ecolab Inc.,; St. Paul, MN Working Example #10

Table 10 illustrates the inclusion of the claimed invention as an antimicrobial agent in hand wash and surgical scrub compositions. As in earlier examples, the data confirms the indicating color formation which has been previously shown to equate to microbial efficacy. All of the colorless, to slightly-colored, starting formulations yielded very obvious self-indicating colored complexes over time. More importantly, the data demonstrates the remarkable ability to formulate the complex within mixtures of cationic, nonionic, amphoteric, and anionic surfactant moieties; a characteristic often lost with conventional antimicrobial compositions.

TABLE 10

| Formulation # | Surfactant Classes | liquid soap color[1] (initial) | liquid soap color[1] (30 seconds) |
|---|---|---|---|
| 1 Formula II | amphoteric | faint yellow | dark orangish |
| 1 Formula X | cationic anionic | colorless | orange-yellow |
| 2 Formula XV | amphoteric nonionic | colorless | bright yellow |
| 3 Formula XVIII | amphoteric anionic | colorless | yellow |
| 4 Formula VI | amphoteric | faint yellow | dark yellow |
| 5 Formula XIX | cationic | light orange | dark orange |

[1]Color formation after 30 seconds of hand scrubbing the 2-part liquid formulations or the solid formulations after mixing with water.

Working Example #11

Table 11 is included as an illustration of several complexes using the present invention. The data is included as a non-exhaustive example of the types of complexes available.

TABLE 11

| | Nitrogen Source | in-situ antimicrobial and antiviral complex (halogen molar ratio) | in-situ complex Comments |
|---|---|---|---|
| 1 | choline | $R^aN^{+\ -}(ClBr_2)$ | dark orange-red liquid |
| 2 | choline | $RN^{+\ -}(ClBr_4)$ | dark orange-red liquid |
| 3 | choline | $RN^{+\ -}(ClI_2)$ | dark brown liquid |
| 4 | choline | $RN^{+\ -}(ClI_4)$ | dark brown liquid |
| 5 | choline | $RN^{+\ -}(ClI_6)$ | dark brown liquid |
| 6 | choline | $RN^{+\ -}(ClI_8)$ | dark brown liquid |
| 7 | choline | $RN^{+\ -}(I_3)$ | dark brown liquid |
| 8 | formula XIX | $RN^{+\ -}(I_3)$ | light orange solid |
| 9 | formula I | $RN^{+\ -}(I_3)$ | brown speckled powder |
| 10 | TBAS[b] | $RN^{+\ -}(I_7)$ | orange liquid |
| 11 | TBAA[c] | $RN^{+\ -}(I_7)$ | orange liquid |

[a]R = choline chloride
[b]TBAS = tributyl ammonium sulfate
[c]TBAA = tributyl ammonium acetate Working Example #12

Table 12 demonstrates additional data for various 2 part liquid formulations, according to the invention, in affecting microbial reduction for: a gram positive and gram negative bacteria, a yeast, and a mold. Results recorded include the pH of the solution, the color of the solution and the log reduction in microbe.

TABLE 12

| Composition | N-source: $H_2O_2$: KI (ppm: ppm:ppm) | pH | Composition Color | Microbe | Log Reduction[b] |
|---|---|---|---|---|---|
| Compositional Controls[c] | | | | | |
| 1 $H_2O_2$ | 0:300:0 | 5 | colorless | E. coli | 0.2 |
| $H_2O_2$ | 0:300:0 | 5 | colorless | S. aureus | 0.4 |
| $H_2O_2$ | 0:532:0 | 3 | colorless | Z. bailii | 0.1 |
| $H_2O_2$ | 0:532:0 | 5 | colorless | Z. bailii | 0.1 |
| $H_2O_2$ | 0:532:0 | 7 | colorless | Z. bailii | 0.1 |
| $H_2O_2$ | 0:532:0 | 5 | colorless | P. expansum | 0.0* |
| $H_2O_2$:KI | 0:250:250 | 5 | colorless | P. expansum | 1.2* |

TABLE 12-continued

| Composition | N-source: $H_2O_2$: KI (ppm: ppm:ppm) | pH | Composition Color | Microbe | Log Reduction b |
|---|---|---|---|---|---|
| KI | 0:0:500 | 5 | colorless | P. expansum | 0.0* |
| 2 choline | 300:0:0 | 7 | colorless | E. coli | 0.0 |
| chloride | 300:0:0 | 7 | colorless | Z. bailii | 0.0 |
| QUAT | 100:0:0 | 7 | colorless | P. expansum | 1.0* |
| (didecyl | 20:0:0 | 3 | colorless | Z. bailii | 0.1 |
| dimethyl ammonium chloride) | 20:432:0 | 3 | colorless | Z. bailii | 0.1 |
| Ternary Compositions | | | | | |
| 3 choline: $H_2O_2$:KI | 100:300:100 | 3 | yellow | S. aureus | >5.2 |
| choline: $H_2O_2$:KI | 100:300:100 | 5 | yellow | S. aureus | >4.7 |
| lecithin: $H_2O_2$:KI | 100:300:100 | 3 | yellow | S. aureus | 4.7 |
| lecithin: $H_2O_2$:KI | 100:300:100 | 5 | yellow | S. aureus | 4.9 |
| lecithin: $H_2O_2$:KI | 100:300:100 | 7 | colorless | S. aureus | 0.0 |
| lecithin: $H_2O_2$:KI | 100:300:100 | 9 | colorless | S. aureus | 0.0 |
| lecithin: $H_2O_2$:KI | 100:25:100 | 3 | yellow | E. coli | 3.1 |
| lecithin: $H_2O_2$:KI | 100:100:100 | 3 | yellow | E. coli | 5.2 |
| lecithin: $H_2O_2$:KI | 100:500:100 | 3 | yellow | E. coli | 5.9 |
| lecithin: $H_2O_2$:KI | 100:300:100 | 7 | colorless | E. coli | 0.3 |
| mix[d]: $H_2O_2$:KI | 100:300:100 | 3 | yellow | S. aureus | >5.2 |
| mix[d]: $H_2O_2$:KI | 100:300:100 | 5 | yellow | S. aureus | 4.4 |
| mix[d]: R2O2:KI | 100:300:100 | 3 | yellow | E. coli | >5.2 |
| mix[d]: $H_2O_2$:KI | 100:300:100 | 5 | yellow | E. coli | 3.8 |
| choline: $H_2O_2$:KI | 100:300:100 | 3 | yellow | Z. bailii | >6.0 |
| betaine: $H_2O_2$:KI | 100:300:100 | 7 | yellow | E. coli | 3.6 |
| QUAT (didecyl dimethyl ammonium chloride) | 50:150:50 20:150:100 10:407:20[e] | 6 3 3 | yellow yellow yellow | P. expansum Z. bailii Z. bailii | >4.6* >6.0 >4.7 |

[a]Nitrogen = natural source of quaternary or protonizable nitrogen.
[b]Log Reduction vs. an untreated control, 30 second contact time except (*) = 15 minute contact time.
[c]Not including added acid or base for pH adjustment.
[d]An equal weight percent mix of lecithin and choline chloride.
[e]Oxidant supplied as peracetic acid/hydrogen peroxide blend.

As shown in Table 12, there is a direct correlation between color of the solution and microbial efficacy for bacteria, yeasts, and molds. In this we are defining a lack of microbial efficacy to be less than a 0.5 log reduction, while effectiveness is being defined as greater a than 1.0 log reduction. Further, Table 5 indicates that the most effective pH appears to be below about 9, with a preferred pH range of about 2 to 8.

Working Example #13

Working Example 13 shows the results of the present invention and known commercial compositions for control of microorganisms on animal tissue surfaces.

Testing was performed on prerigor beef tissue surfaces from a packing house. Total bacterial flora were tested. The carcasses were treated for 30 seconds and drained for 10 minutes. Test samples were isolated and plated for total call in the former units.

TABLE 13

| Test # | Treatment Process | Active Antimicrobial | Log Reduction[a] |
|---|---|---|---|
| | Known | | |
| 1 | lactic acid | 5000 ppm | 0.8 |
| 2 | cetyl pyridinium chloride | 1000 ppm | 0.5 |
| 3 | Citrex[b] | 1880 ppm | 0.7 |
| 4 | fatty acid blend[c] | 500 ppm | 1.7 |
| 5 | peracid[d] | 500 ppm | 1.4 |
| | Present Invention | | |
| 6 | cetyl pyridinium chloride + $H_2O_2$ + KI | 50 ppm | 2.0 |

[a]Log Reduction relative to the untreated starting meat carcass.
[b]Commercial product from Citrex, Inc.; Miami, Florida.
[c]U.S. Pat. No. 5,200,189; Ecolab, Inc.; St. Paul, MN using C8/C10 fatty acids.
[d]Tsuanmi[R]; Ecolab, Inc.; St. Paul, MN using C2/C8 peracids.

The results of Table 13 demonstrate the remarkably improved effectiveness of the current composition versus the conventional chemical treatments. Log reductions for the present composition was above any of the commercial treatments while using ten to one hundred times lower concentrations of actives.

Working Example #14

The data of table 14 illustrates the microbial reduction effectiveness of a powdered formula according to the present invention. The powder composition of Formula XXVII (previously described) was tested for microbial efficacy. Six grams of the powdered formula was dissolved into one gallon of water containing 500 ppm of synthetic hardness (equal mix of calcium and magnesium carbonates) and the resultant solution was tested for efficacy against the gram-negative bacteria *Esherichia coli* (*E. coli*) ATCC 1129 at various time periods after preparation. Thirty second exposure times were used, and the microbial platings were performed per Ecolab Microbiological Services SOP method MS009 (reference: AOAC Method 960.09); i.e., thirty second exposure times were used and 1 mL of the test substance/microorganism mixture was transferred into 9.0 mL of neutralizer for a $10^{-1}$ dilution. Subsequent dilutions were made using sterile phosphate buffered dilution water to yield dilutions of $10^{-3}$, and $10^{-5}$. Pour plate technique was utilized with Tryptone Glucose Extract agar and plates were incubated at 37° C. for 48 hours.

The results demonstrate the extended efficacy of the powder formula against the common food or water contaminant *E. coli*, even in the presence of considerable water hardness. This result is surprising since it is common knowledge in the art that hardness ions severely interfere with conventional quaternary ammonium halide antimicrobials. No detrimental effect is found in the current study. The previously demonstrated correlation between color, titratable actives, and microbial kill is seen again; i.e., no color or titratable actives yields no microbial reduction, while titratable actives and color correspond to reduction. The actives were titrated using an Ecolab test kit #101 using thiosulfate to titrate active iodine levels at 1 ppm per drop of titrant. The formula mix time and microbial testing was not followed to a time that would demonstrate a loss in log reduction with loss in titratable actives; however, the next example using a more tenacious microbe will show this expected result.

TABLE 14

| Formula Mix Time[1] (hours) | Solution Color | Titratable Active[2] (ppm) | Microbial Counts (CFU/ml) | Log Reduction[3] (E. coli) |
|---|---|---|---|---|
| 0 | colorless | 0 | 6 × 10$^7$ | 0 |
| 0.1 | yellow | 10 | <10 | 6.9 |
| 8 | yellow | 15 | <10 | 6.9 |
| 24 | yellow | 20 | <10 | 7.0 |
| 32 | yellow | 20 | <10 | 7.0 |
| 48 | yellow | 12 | <10 | 7.0 |

[1] The time elapsed after mixing the formula powder into the test solution.
[2] Titratable active oxidant using test kit #101.
[3] Relative to an untreated control standard using SOP#MS009.

Working Example #15

As in example 14, the data of Table 15 illustrates the microbial reduction effectiveness of a powdered formula according to the present invention. The test protocol of example 14 was used and the resultant solution was tested for efficacy against the gram-positive bacteria *Staphylococcus aureus* ATCC 6538, another common human pathogen on food matter or in wash waters.

Again, the results demonstrate the microbial efficacy of the powder compositions. Additionally, they teach the correlation between reduction effectiveness and titratable actives; i.e., ranging from no reduction with 0 titratables, to near 4-log reduction with 20 ppm titratables, and then back to near 3-log reduction with 12 ppm. This demonstrates the gaussian kill profile of the formula with the desired fall-off of actives over time.

TABLE 15

| Formula Mix Time[1] (hours) | Solution Color | Titratable Active[2] (ppm) | Microbial Counts (CFU/ml) | Log Reduction[3] (S. aureus) |
|---|---|---|---|---|
| 0 | colorless | 0 | 6 × 10$^7$ | 0 |
| 0.1 | yellow | 10 | 5 × 10$^5$ | 2.1 |
| 8 | yellow | 15 | 4 × 10$^4$ | 3.2 |
| 24 | yellow | 20 | 9 × 10$^3$ | 3.9 |
| 32 | yellow | 20 | 1 × 10$^4$ | 3.7 |
| 48 | yellow | 12 | 5 × 10$^4$ | 3.2 |

[1] The time elapsed after mixing the formula powder into the test solution.
[2] Titratable active oxidant using test kit #101.
[3] Relative to an untreated control standard using SOP#MS009.

Working Example #16

Table 16 presents the effect of pH in affecting microbial reduction using a protonizable amphoteric for a variety of microbes. Results recorded include the pH of the solution, the color of the solution and the log reduction in microbes.

Again, the results demonstrate the correlation between the use solution color and microbial reduction for a variety of bacteria types; i.e., with the yellow coloration induced by the complex, microbial reduction occurs. In contrast to Kramer et al., U.S. Pat. No. 4,941,989; and Kramer et al., U.S. Pat. No. 5,620,527, which teach the use of antimicrobial compositions made of alkaline per-salts of quaternary ammonium compounds and hydroperoxide (i.e., HOO$^-$) anions at pH's of greater than 9.5, the results demonstrate the novelty of the current invention by the enhanced microbial kill profiles at pH's while using less aggressive pH's below about 9. The data also indicates that the maximum kill profile occurs for a weight ratio of [nitrogen source:hydrogen peroxide:iodide] at about [1:1:1 to about 1:5:1] (or higher for the peroxide).

TABLE 16

| | Composition amphoteric[1]:H$_2$O$_2$:KI (ppm:ppm:ppm) | pH | Composition Color | Microbe | Log Reduction[2] |
|---|---|---|---|---|---|
| 1 | 100:25:100 | 3 | yellow | S. aureus | 2.9 |
| | | 3 | yellow | P. aeruginosa | >7.3 |
| | | 3 | yellow | K. pneumoniae | >6.9 |
| 1 | 100:25:100 | 9.1 | colorless | S. aureus | <0.5 |
| | | 9.1 | colorless | P. aeruginosa | <0.5 |
| | | 9.1 | colorless | K. pneumoniae | <0.5 |
| 2 | 100:50:100 | 3 | yellow | S. aureus | 3.3 |
| | | 3 | yellow | P. aeruginosa | >7.3 |
| | | 3 | yellow | K. pneumoniae | >6.9 |
| 2 | 100:50:100 | 9.1 | colorless | S. aureus | <0.5 |
| | | 9.1 | colorless | P. aeruginosa | <0.6 |
| | | 9.1 | colorless | K. pneumoniae | 0.5 |
| 3 | 100:100:100 | 3 | yellow | S. aureus | 3.9 |
| | | 3 | yellow | P. aeruginosa | >7.3 |
| | | 3 | yellow | K. pneumoniae | >6.9 |
| 3 | 100:100:100 | 9.1 | colorless | S. aureus | <0.5 |
| | | 9.1 | colorless | P. aeruginosa | <0.6 |
| | | 9.1 | colorless | K. pneumoniae | <0.5 |
| 4 | 100:300:100 | 3 | yellow | S. aureus | >6.7 |
| | | 3 | yellow | P. aeruginosa | >7.3 |
| | | 3 | yellow | K. pneumoniae | >6.9 |
| 4 | 100:300:100 | 9.1 | colorless | S. aureus | 0.5 |
| | | 9.1 | colorless | P. aeruginosa | <0.7 |
| | | 9.1 | colorless | K. pneumoniae | <0.6 |
| 5 | 100:500:100 | 3 | yellow | S. aureus | >6.7 |
| | | 3 | yellow | P. aeruginosa | >7.3 |
| | | 3 | yellow | K. pneumoniae | >6.9 |
| 5 | 100:500:100 | 9.1 | colorless | S. aureus | 0.5 |
| | | 9.1 | colorless | P. aeruginosa | <0.7 |
| | | 9.1 | colorless | K. pneumoniae | <0.6 |

[1] The amphoteric is Miranol CEM-38 from Rhone Poulenc.
[2] Log reduction vs. an untreated control.

Working Example #17

The data of Table 17 illustrates the microbial reduction effectiveness of various solid and 2-part liquid compositions for sanitizing food preparation or consumption utensils in a sink; as styled in the restaurant industry as "third-sink-sanitizing" applications.

A previously described powder composition and various liquid compositions were prepared and tested for: evidencing color formation, titratable active components using a chlorine equivalence (as per kitchen health standard guidelines), and microbial efficacy. The indicated dosages were dissolved into one gallon of water and the resultant solutions were tested for efficacy as per active oxidant using test kit #101, visual production of the yellowish indicating color, and microbial plating.

The results indicated the developing onset of the yellow color, a titratable active component forming over time, and an appreciable microbial reduction for a variety of microorganisms including gram positive and gram negative bacteria and a yeast. Again, and equally important, is the previously considered resiliency to hardness ions which are known to severely interfere with conventional quaternary ammonium halide antimicrobials. No detrimental effect is found in the current study.

TABLE 17

| Test Composition | Added Weight (grams) | Solution Color[1] | 30 Minute Titratable Active[2] (ppm) | Microbe Tested | [30 Second] Log Reduction[3] |
|---|---|---|---|---|---|
| powder XXVII | 4.2 | t = 0, colorless<br>t = 5 min., yellow<br>t = 30 min., yellow | 20 ppm | E. coli | >5.2 |
| powder XXVII | 4.2 | t = 0, colorless<br>t = 5 min., yellow<br>t = 30 min., yellow | 20 ppm | S. aureus | >4.7 |
| liquid XI | 18.9 | t = 0, colorless<br>t = 5 min., yellow<br>t = 30 min., yellow | not tested | E. coli | >7.0 |
| liquid XII | 3.8 | t = 0, colorless<br>t = 5 min., yellow<br>t = 30 min., yellow | 49 ppm | Z. bailii | >6.0 |
| liquid XIII | 37.9 | t = 0, colorless<br>t = 5 min., yellow<br>t = 30 min., yellow | 120 ppm | Z. bailii | >4.7 |
| liquid XIV | 37.9 | t = 0, colorless<br>t = 5 min., yellow<br>t = 30 min., yellow | 125 ppm | Z. bailii | >4.7 |
| liquid XVI | 3.8 | t = 0, colorless<br>t = 5 min., yellow<br>t = 30 min., yellow | not tested | E. coli | 6.0 |

[1]The time elapsed after mixing the formula powder into the test solution.
[2]Titratable active oxidant using test kit #101.
[3]Relative to an untreated control standard using SOP#MS009, using a 30 second exposure time after 5 minutes of complex formation.

Working Example #18

The data of Table 18 demonstrates the storage stability, for effecting microbial reduction, of a powdered formula (Formula XXVII) according to the present invention; i.e., storage stability of the current invention while in a powder form. The test protocol of example 14 was used, except using 12 grams per gallon of the powder Formula XXVII, and the resultant solution was tested for efficacy against *Staphylococcus aureus* ATCC 6538.

The results of Table 18 demonstrate the microbial efficacy of the powder compositions, even over an extended storage time.

TABLE 18

| Formula XXVII Powder Age[1] (days) | Solution Color | 30 second Log Reduction[2] (S. aureus) |
|---|---|---|
| 0 days | yellow | 0 |
| 15 days | yellow | >6.8 |
| 30 days | yellow | >6.9 |
| 150 days | yellow | >6.8 |

[1]The aging time elapsed from the production date of a powder Formula XXVII.
[2]Relative to an untreated control standard using SOP#MS009.

Working Example #19

The data of Table 19 demonstrates the hospital disinfectant efficacy of the powdered Formula XXVII according to the present invention. The Use Dilution Method (as outlined in AOAC Methods 955.14, 955.15, and 964.02 [15th ed., 1990]) was used to determine the effectiveness of the present invention for hard surface disinfection. The results using the most robust organism of the test method, *Pseudomonas aeruginosa* ATCC 15442 are shown.

The results of Table 19 demonstrate the microbial efficacy of the powder compositions at three concentrations; with a concentration of 32 grams per gallon passing on all 60 of 60 tubes tested.

TABLE 19

| Formula XXVII Use Concentrations (grams per gallon) | Solution Color | # of Negative Tubes per # of Tubes Tested[1] (P. aeruginosa) |
|---|---|---|
| 0 | colorless | 0/60 |
| 12 g/gallon | yellow | 17/60 |
| 24 g/gallon | yellow | 57/60 |
| 32 g/gallon | yellow | 60/60 |

[1]59–60/60 required for passing disinfection claim.

Working Example #20

An antimicrobial wash powder for use in reducing microbial counts on food matter, in food process waters, warewash machines, and third-sink sanitizing was made by mixing together, at ambient temperature: 77.3 g sodium dihydrogen phosphate, 18.8 g sodium percarbonate, 2.6 g KI, and 1.3 g choline chloride to afford a white powder. Dilution of 0.4 g powder in 1000 g water afforded a pale yellow solution with a pH of 6.6 which is effective for food washing and wash waters.

Working Example #21

A germicidal block for use in reducing microbial counts on food matter, in food process waters, warewash machines, and third sink sanitizing was made by mixing together, at ambient temperature: 724.9 g sodium tripoly phosphate, 57.0 g choline chloride, 115.0 g KI, and while still mixing, adding 295.9 g hydrogen peroxide [35% active] dropwise to minimize effects of strong exotherm which develops. At end of peroxide addition, product was a dark orange, damp powder which was transferred to a mold for solidification. Solidification to a very hard block occurred within 1 minute of transfer to the mold. Flushing or spraying water over block affords a pale yellow solution which is effective for food washing, wash waters, and sanitizing.

Working Example #22

A germicidal block for use in reducing microbial counts on food matter, in food process waters, warewash machines, and third sink sanitizing was made by mixing together, at ambient temperature: 724.9 g sodium tripoly phosphate, 57.0 g choline chloride, 115.0 g KI, and while still mixing, adding 295.9 g hydrogen peroxide [35% active] dropwise to minimize effects of strong exotherm which develops. At end of peroxide addition, product was a dark orange, damp powder which was transferred to a mold for solidification. Solidification to a very hard block occurred within 1 minute of transfer to the mold. Flushing or spraying water over block affords a pale yellow solution which (with a titratable residual and the distinctive 365 nm peak for the complex) is effective for food washing, wash waters, and sanitizing.

Working Example #23

A germicidal oil-soluble for use in reducing microbial counts on food matter, in food process waters, warewash machines, third sink sanitizing, non-aqueous lubricants, and mammalian skin surfaces was made by mixing together, at ambient temperature: 30 grams of a hydrophobic oil (like food-grade mineral oil, linoleic acid, or soy oil), 10.0 g lecithin, and 2.0 g iodine. Almost immediately the typifying yellow color of the active composition forms. The formulation can be thickened with common thickeners. It is used as a non-aqueous treatment, or subsequently added to other products as an antimicrobial or antiviral additive.

Working Example #24

The germicidal powder of Formula VIIb for use in reducing microbial counts on food matter, in food process waters, warewash machines, third sink sanitizing, and veterinarian applications was made by mixing together, at ambient temperature: 193.25 g sodium dihydrogen phosphate, 193.25 g citric acid, 94.00 g sodium percarbonate, 13.00 g potassium iodide, and 6.50 g choline chloride. Mixed together the formula yields a white powder with yellow & brown particles. Mixing 6 grams per gallon of the formula into water yields a yellow color after 30 seconds with the distinctive 365 nm peak corresponding to the claimed active.

Working Example #25

A germicidal block for use in reducing microbial counts, as described in the earlier examples, is made by mixing together at ambient temperature 127.55 g dipotassium hydrogen phosphate, 258.95 g citric acid, 18.80 g sodium percarbonate, 2.60 g potassium iodide, and 6.50 g choline chloride; followed by placing the mix into a block mold and into a 120° F. oven for 12 hours to solidify to a hard, light orange, block. Flushing or spraying water over the block affords a pale yellow solution (with a titratable residual and the distinctive 365 nm peak for the complex) which is effective for food washing, wash waters, and sanitizing.

Working Example #26

A germicidal powder for use in reducing microbial counts on food matter, in food process waters, warewash machines, third sink sanitizing, and veterinarian applications was made by mixing together, at ambient temperature: 38.65 g citric acid, 38.65 g sodium diacetate, 18.8 g sodium percarbonate, 1.3 g potassium iodide, and 1.3 g choline chloride. Mixed together the formula yields a white powder. Mixing 6 grams per gallon of the formula into water yields a yellow color after 30 seconds with the distinctive 365 nm peak corresponding to the claimed active.

Working Example #27

Preparation of Choline Tetraiodochloride: Mixed together 50.18 g choline chloride and 91.3 g iodine at ambient temperature. As the desired complex formed during mixing, the white powder of the choline chloride and the gray flakes of the iodine became a dark brown liquid. It was unexpected that a cationic material such as our target product was a solvent-free liquid rather than a solid.

Working Example #28

Preparation of Choline Diiodochloride: Mixed together 100.0 g choline chloride and 181.6 g iodine at ambient temperature. As the desired complex formed during mixing, the white powder of the choline chloride and the gray flakes of the iodine became a dark brown liquid. It was unexpected that a cationic material such as our target product was a solvent-free liquid rather than a solid.

Working Example #29

A germicidal block for use in reducing microbial counts is made by mixing together at 70° C. 9.8 g Grindsted Citrem N12 [stearyl citrate; supplier: Danisco] and 0.2 g of the choline diiodochloride made in example #22; followed by placing the mix into a block mold and cooling to room temperature to a hard, light orange, block. Flushing or spraying water over the block affords a pale yellow solution (with a titratable residual and the distinctive 365 nm peak for the complex) which is effective for food washing, wash waters, and sanitizing.

Working Example #30

A germicidal block for use in reducing microbial counts is made by melting together at about 60° C. 16.3 g polyethylene glycol (PEG) 6000 distearate and 0.3 g of the choline diiodochloride—as made in example #22—followed by placing the mix into a block mold and cooling to room temperature to a hard, tan block. Flushing or spraying water over the block affords a pale yellow solution (with a titratable residual and the distinctive 365 nm peak for the complex) which is effective for food washing, wash waters, and sanitizing.

Working Example #31

A germicidal block for use in reducing microbial counts is made by melting together at about 60° C. 50.0 g polyethylene glycol (PEG) 6000 distearate, 14.5 g citric acid, and 1.5 g of the choline diiodochloride—as made in example #22—followed by placing the mix into a block mold and cooling to room temperature to a hard, yellow block. Flushing or spraying water over the block affords a pale yellow solution (with a titratable residual and the distinctive 365 nm peak for the complex) which is effective for food washing, wash waters, and sanitizing.

Working Example #32

A germicidal block for use in reducing microbial counts is made by melting together at about 60° C. 50.0 g polyethylene glycol (PEG) 6000 distearate, 14.5 g citric acid, and 1.5 g of the choline diiodochloride—as made in example #22—followed by placing the mix into a block mold and cooling to room temperature to a hard, yellow block. Flushing or spraying water over the block affords a pale yellow solution (with a titratable residual and the distinctive 365 nm peak for the complex) which is effective for food washing, wash waters, and sanitizing.

Working Example #33

A germicidal block for use in reducing microbial counts is made by mixing without heat 41.43 g trisodium phosphate dodecahydrate, 10.00 g citric acid, and 2.00 g of the choline diiodochloride—as made in example #22—followed by pressing the mix into a block mold and cooling to room temperature to a hard, white block. Flushing or spraying water over the block affords a pale yellow solution (with a titratable residual and the distinctive 365 nm peak for the complex) which is effective for food washing, wash waters, and sanitizing.

Working Example #34

Preparation of Choline Dibromochloride: Mixed together in the absence of solvent to afford an orange-red gel: 8.28 g choline chloride and 4.73 g bromine. The gel can be used as a surface antimicrobial, or as an additive to other compositions and products.

Working Example #35

Preparation of Choline Tetrabromochloride: Mixed together in the absence of solvent to afford an orange-red liquid: 1.72 g choline chloride and 1.96 g bromine. The solventless liquid can be used as a surface antimicrobial, or as an additive to other compositions and products. Especially useful is to deposit the pre-made complex onto a water soluble or dispersible substrate for rapid water release.

Working Example #36

Preparation of Choline Tetraiodochloride: Mixed together in the absence of solvent and warmed gently for a few minutes in a 120F. oven to afford a solvent-free, dark brown liquid: 5.0 g choline chloride, 18.1 g iodine. The solventless liquid can be used as a surface antimicrobial, or as an additive to other compositions and products. Especially useful is to deposit the pre-made complex onto a water soluble or dispersible substrate for rapid water release.

Working Example #37

Preparation of Choline Hexaiodochloride: Mixed together in the absence of solvent and warmed gently for a few minutes in a 120F oven to afford a solvent-free, dark brown liquid: 5.0 g choline chloride and 27.2 g iodine. The solventless liquid can be used as a surface antimicrobial, or as an additive to other compositions and products. Especially useful is to deposit the pre-made complex onto a water soluble or dispersible substrate for rapid water release.

Working Example #38

Preparation of Choline Octaiodochloride: Mixed together in the absence of solvent and warmed gently for a few minutes in a 120F oven to afford a solvent-free, dark brown liquid: 5.0 g choline chloride, 36.3 g iodine. The solventless liquid can be used as a surface antimicrobial, or as an additive to other compositions and products. Especially useful is to deposit the pre-made complex onto a water soluble or dispersible substrate for rapid water release.

Working Example #39

A germicidal and antiviral block for use as a laundry sour and sanitizer was made by melting together at 70° C.: 7.7 g PEG-550, 46.1 g of succinic acid, 0.1 g silicone antifoam, 3.0 g sodium bisulfate, 0.2 g fragrance, 2.4 g dimethyl distearyl ammonium chloride, and 1.4 g choline diiodochloride; followed by pouring the mix into a block mold for 2 hours to solidify to a hard, light orange block. Flushing or spraying water over the block affords a pale yellow solution (with a titratable residual and the distinctive 365 nm peak for the complex) which is effective for food washing, wash waters, and sanitizing.

Working Example #40

Four germicidal and antiviral two-part laundry sanitizing detergents were made by mixing together, at ambient temperature the following formulas as shown in part A. These formulae were used at 0.2 wt % in water as a wash followed by addition, in the same step or a subsequent step, of 200 ppm of part B for sanitizing. The use solution from part A was colorless in the wash step, but with the addition of part B the solution formed a yellow-titratable solution with the indicated formation of the iodine complex.

| | Component | Formula 1A | Formula 1B | Formula 1C | Formula 1D |
|---|---|---|---|---|---|
| Part A: | 5-EO alcohol ethoxlylate | 0 | 35.72 | 0 | 35.72 |
| | 7-EO alcohol ethoxylate | 0 | 35.72 | 0 | 35.72 |
| | nonylphenol ethoxylate 4.5 | 35.72 | 0 | 35.72 | 0 |
| | nonylphenol ethoxylate 9.5 | 35.72 | 0 | 35.72 | 0 |
| | Monateric CEM[1] | 12.00 | 12.00 | 12.00 | 12.00 |
| | butyl cellosolve | 11.56 | 11.56 | 11.56 | 11.56 |
| | sodium iodide | 5.00 | 5.00 | 5.00 | 5.00 |
| | optical brightener | 0 | 0 | 0.06 | 0.06 |
| Part B: | hydrogen peroxide (35%) | | | | |

[1]Mona Industries 38.65 g citric acid, 38.65 g sodium diacetate, 18.8 g sodium percarbonate, 1.3 g potassium iodide, and 1.3 g choline chloride. Mixed together, the formula yields a white powder. Mixing 6 grams per gallon of the formula into water yields a yellow color after 30 seconds with the distinctive 365 nm peak corresponding to the claimed active.

The above specification, examples and data provide a complete description of the manufacture and use of the composition of the invention. Since many embodiments of the invention can be made without departing from the spirit and scope of the invention, the invention resides in the claims hereinafter appended.

We claim:

1. An antimicrobial or antiviral composition comprising a combination of:

(a) a nitrogen compound selected from an alkyl piperidinium salt, phosphatidylcholine, choline chloride, choline tartrate, choline acetate, and a mixture thereof;

(b) an oxidant; and (c) a halide source comprising a metal halide salt, a halogen or a mixture thereof, wherein said halide or halogen comprises at least a bromine or iodine atom.

2. The composition of claim 1, wherein the quaternary nitrogen compound is an alkyl piperidinium salt.

3. The composition of claim 1, wherein the nitrogen compound is from a natural source, and is phosphatidylcholine, choline chloride, choline tartrate, choline acetate, or a mixture thereof.

* * * * *